(12) United States Patent
Vlassov et al.

(10) Patent No.: US 8,901,284 B2
(45) Date of Patent: Dec. 2, 2014

(54) METHODS AND COMPOSITIONS FOR EXOSOME ISOLATION

(71) Applicant: Life Technologies Corporation, Carlsbad, CA (US)

(72) Inventors: Alexander Vlassov, Austin, TX (US); Mu Li, Austin, TX (US); Emily Zeringer, Austin, TX (US); Richard Conrad, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/191,109

(22) Filed: Feb. 26, 2014

(65) Prior Publication Data

US 2014/0178888 A1 Jun. 26, 2014

Related U.S. Application Data

(63) Continuation of application No. 13/765,677, filed on Feb. 12, 2013, now abandoned.

(60) Provisional application No. 61/625,562, filed on Apr. 17, 2012.

(51) Int. Cl.
| | |
|---|---|
| *C07K 1/30* | (2006.01) |
| *C12Q 1/68* | (2006.01) |
| *G01N 1/34* | (2006.01) |
| *G01N 33/50* | (2006.01) |

(52) U.S. Cl.
CPC ............. *C12Q 1/6806* (2013.01); *G01N 1/34* (2013.01); *G01N 33/5005* (2013.01); *G01N 33/5076* (2013.01)
USPC .......................................... 530/421; 435/6.1

(58) Field of Classification Search
None
See application file for complete search history.

(56) References Cited

U.S. PATENT DOCUMENTS

2013/0273544 A1 10/2013 Vlassov et al.
2013/0337440 A1* 12/2013 Antes et al. ............ 435/6.1

FOREIGN PATENT DOCUMENTS

WO WO 2013/158203 10/2013

OTHER PUBLICATIONS

Wu, F. et al., "An exosome isolation system for serum-bsed cancer biomarker discovery", AACR 101st Annual meeting, Apr. 20, 2010, 1 page (abstract).*

Adams, "Concentration of Epstein-Barr virus from cell culture fluids with polyethylene glycol", *Journal of General Virology*, vol. 20, No. 3, Sep. 1973, 391-394.
Cheruvanky et al., "Rapid isolation of urinary exosomal biomarkers using a nanomembrane ultrafiltration concentrator", *American Journal of Physiology, Renal Physiology*, vol. 292, No. 5, May 2007, F1657-F1661.
International Application No. PCT/US2013/025844, , International Search Report and Written Opinion mailed Apr. 19, 2013, 1-12.
Kosaka et al., "microRNA as a new immune-regulatory agent in breast milk", *Silence*, vol. 1, No. 7, 2010, 1-8.
Lewis et al., "Polyethylene glycol precipitation for recovery of pathogenic viruses, including hepatitis A virus and human rotavirus, from oyster, water, and sediment samples", *Applied and Environmental Microbiology*, vol. 54, No. 8, 1983-1988, 1988.
Mitchell et al., "Circulating microRNAs as stable blood-based markers for cancer detection", *Proceedings of the National Academy of Sciences*, vol. 105, No. 30, Jul. 29, 2008, 10513-10518.
Mittelbrunn et al., "Intercellular communication: diverse structures for exchange of genetic information", *Nature Review Molecular & Cellular Biology*, vol. 13, No. 5, Apr. 18, 2012, 328-335.
Palanisamy et al., "Nanostructural and Transcriptomic Analyses of Human Saliva Derived Exosomes", *PLos One*, vol. 5, No. 1, Jan. 2010, e8577.
System Biosciences Inc., "Exosome Research", Jan. 1, 2013, 1-7.
Taylor et al., "Exosome Isolation for Proteomic Analyses and RNA Profiling", *Molecular Biology*, vol. 728, Chapter 15, 2011, 235-246.
Thery et al., "Exosomes: composition, biogenesis and function", *Nature Reviews: Immunology*, vol. 2, Aug. 2002, 569-579.
Thery et al., "Isolation and Characterization of Exosomes from Cell Culture Supernatants and Biological Fluids", *Current Protocols in Cell Biology*, Unit 3, Section 22, Supplement 30, 2006, 1-29.
Valadi et al., "Exosome-mediated transfer of mRNAs and microRNAs is a novel mechanism of genetic exchange between cells.", *Nature: Cell Biology*, vol. 9, No. 6, May 7, 2007, 654-659.
Vlassov et al., "Exosomes: Current knowledge of their comparison, biological functions, and diagnostic and therepeutic potentials", *Biochimica et Biophysica Acta*, vol. 1820, No. 7, Apr. 1, 2012, 940-948.
Wang et al., *Nucleic Acids Research*, vol. 38, No. 20, 2010, 7248-7259.
Yamamoto et al., "Rapid bacteriophage sedimentation in the presence of polyethylene glycol and its application to large-scale virus purification", *Virology*, vol. 40, No. 3, Mar. 1970, 734-744.
Invitrogen, Total Exosome Isolation (from Cell culture media), Publication No. MAN0006949, Catalog No. 4478359, Jun. 28, 2012, 1-2.

* cited by examiner

*Primary Examiner* — Michael Burkhart

(57) ABSTRACT

Disclosed are methods, compositions and kits for the isolation of exosomes from biological fluids and tissues. Volume-excluding polymers are used to precipitate exosomes from biological samples thereby allowing exosome isolation by low-speed (benchtop) centrifugation or filtration. Further fractionation of exosomes after precipitation is also described.

20 Claims, 16 Drawing Sheets

METHODS AND COMPOSITIONS FOR EXOSOME ISOLATION

CROSS REFERENCE TO RELATED APPLICATIONS

This application is a continuation of U.S. application Ser. No. 13/765,677 filed Feb. 12, 2013 and claims priority U.S. Application No. 61/625,562 filed Apr. 17, 2012, which disclosures are herein incorporated by reference in their entirety.

FIELD

The disclosure generally relates to the isolation of exosomes from biological tissues and fluids.

BACKGROUND

Cells continuously secrete a large number of microvesicles, nanovesicles, macromolecular complexes, and small molecules into the extracellular space. Exosomes are small secreted vesicles (typically about 30-150 nm) which may contain or have present in their membrane nucleic acid, protein, or other biomolecules and may serve as carriers of this cargo between diverse locations in the body (Mittelbrunn & Sanchez-Madrid, Nature Reviews 13 (2012) 328-335; Thery et al. Nat. Rev. Immunol. 2 (2002) 569-579; Valadi et al. Nat. Cell. Biol. 9 (2007) 654-659). Exosomes are secreted by all types of cells in culture, and also found in abundance in body fluids including blood, saliva, urine, and breast milk (Kosaka et al., Silence 3 (2010) 1-7; Mitchell et al., PNAS 105 (2008) 10513-10518; Palanisamy et al., PLoS One 5 (2010) e8577).

Currently, the control of exosome formation, the makeup of the "cargo", biological pathways and resulting functions are incompletely understood. One of their most intriguing roles is intercellular communication. Exosomes are thought to function as messengers, delivering various effector or signaling macromolecules between cells.

The accepted protocol for isolation of exosomes includes ultracentrifugation (Thery et al., Curr. Protoc. Cell. Biol., Chapter 3, Unit 3: 22 (2006)), often in combination with sucrose density gradients or sucrose cushions to float the relatively low-density exosomes. Isolation of exosomes by sequential differential centrifugations is complicated by the possibility of overlapping size distributions with other microvesicles or macromolecular complexes. Furthermore, centrifugation may provide insufficient means to separate vesicles based on their sizes. However, sequential centrifugations, when combined with sucrose gradient ultracentrifugation, can provide high enrichment of exosomes.

Isolation of exosomes based on size, using alternatives to the ultracentrifugation routes, is another option. Successful purification of exosomes using ultrafiltration procedures that are less time consuming than ultracentrifugation, and do not require use of special equipment have been reported (Cheruvanky et al., J. Physiol. Renal Physiol. 292 (2007) 1657-1661.) Similarly, a commercial kit is available (ExomiR, Bioo Scientific) which allows removal of cells, platelets and cellular debris on one microfilter and capturing of vesicles bigger than 30 nm on a second microfilter using positive pressure to drive the fluid. For this process, the exosomes are not recovered, their RNA content is directly extracted off the material caught on the second microfilter, which can then be used for PCR analysis. HPLC-based protocols could potentially allow one to obtain highly pure exosomes, though these processes require dedicated equipment and are difficult to scale up. A significant problem is that both blood and cell culture media contain large numbers of nanoparticles (some non-vesicular) in the same size range as exosomes. For example, Wang et al. (Nucleic Acids Res. 38 (2010) 7248-7259.) found that large number of miRNAs are contained within extracellular protein complexes rather than exosomes. As a consequence, the above methods are best described as allowing one to obtain exosome-enriched samples, rather than pure exosomes.

Volume-excluding polymers such as PEGs can sometimes be used for precipitation of viruses and other small particles (Yamamoto et al. Virology 40 (1970) 734-744; Adams, J. Gen. Virol. 20 (1973) 391-394; Lewis et al., Applied and Environmental Microbiol. 4 (1988) 1983-1988). We have unexpectedly found that despite exosomes being noticeably less dense than viruses due to the lack of a protein coat and variable, though probably lower (for their size), nucleic acid content, volume-excluding polymers are capable of differentially precipitating exosomes thereby allowing exosome isolation by low-speed (benchtop) centrifugation or filtration.

SUMMARY

Discussed herein are methods and compositions using volume-excluding polymers such as polyethylene glycols (PEG) to precipitate exosomes from biological samples. The precipitated exosomes can be isolated using low-speed centrifugation, filtration or other method for isolating precipitated material. Some embodiments are for a method for the isolation of exosomes from a biological fluid sample comprising: a) adding a volume excluding polymer to the biological fluid sample, b) incubating the biological fluid sample with the volume-excluding polymer, and isolating the aggregated/precipitated exosomes from the biological fluid sample.

In other embodiments, non-limiting examples of volume excluding polymers include polyethylene glycol, a dextran including dextran sulfate and dextran acetate, or a hydrophilic polymer such as polyvinyl alcohol, polyvinyl acetate or polyvinyl sulfate.

In particular embodiments, the volume-excluding polymer has a molecular weight of between 1000 and 1,000,000 daltons, from 3000 to 20000 daltons, from 4000 to 20000 daltons, from 6000 to 20000 daltons, from 1000 to 10000 daltons, from 3000 to 10000 daltons, from 3000 to 8000 daltons, from 4000 to 8000, or from 3000 to 6000 daltons.

In other embodiments, the volume-excluding polymer is added to the biological fluid sample to a final concentration of from 1% to 90%, 2% to 50%, 2% to 20%, 2% to 15%, 2% to 12%, 3% to 15%, 4% to 15%, 6% to 15%, 8% to 15%, 4% to 12%, 6% to 12%, or 8% to 12% (weight/volume).

In some embodiments the biological fluid sample may be clarified prior to the addition of the volume-excluding polymer. Clarification may involve, but is not limited to, centrifugation, ultracentrifugation, filtration, and ultrafiltration.

In other embodiments, biological material may be isolated from the exosomes after they are isolated. Biological materials that may be isolated from exosomes include, but are not limited to, nucleic acids such as RNA, DNA, proteins and peptides.

In further embodiments, non-limiting examples of biological fluid samples include serum, plasma, whole blood, urine, saliva, breast milk, tears, sweat, joint fluid, cerebrospinal fluid, semen, vaginal fluid, ascitic fluid, amniotic fluid, and media taken from cultured cells ("conditioned media"). In some embodiments, the biological fluid sample may be obtained from a mammal such as a mouse, rat, guinea pig, rabbit, dog, cat, bovine, horse, goat, sheep, primate or human.

An alternate embodiment may be a method for the isolation of exosomes from a biological tissue sample comprising: a) lysing the biological tissue sample, b) clarifying the lysed sample, c) adding a volume-excluding polymer to the clarified sample, d) incubating the clarified sample with the volume-excluding polymer, and e) isolating the precipitated exosomes.

In further embodiments, non-limiting examples of biological tissue samples include surgical samples, biopsy samples, tissues, feces, plant tissue, insect tissue, and cultured cells.

In some embodiments, exosomes isolated using a volume-excluding polymer may be further fractionated based on their size, density or proteins exposed on the surface of the exosome.

Some embodiments provide for a kit for the isolation of exosomes from biological fluids or tissues. Kits may comprise one or more vessels containing one or more volume-excluding polymers, one or more buffers or one or more solutions for performing density gradient centrifugation of exosomes. The kit may further comprise a filtration device for separating exosomes by their size. The kit may also comprise one or more antibodies or other ligands which bind to a protein or other ligand exposed on the surface of the exosome and one or more solid supports which bind directly or indirectly to the exosomes.

DETAILED DESCRIPTION

Figure 1:
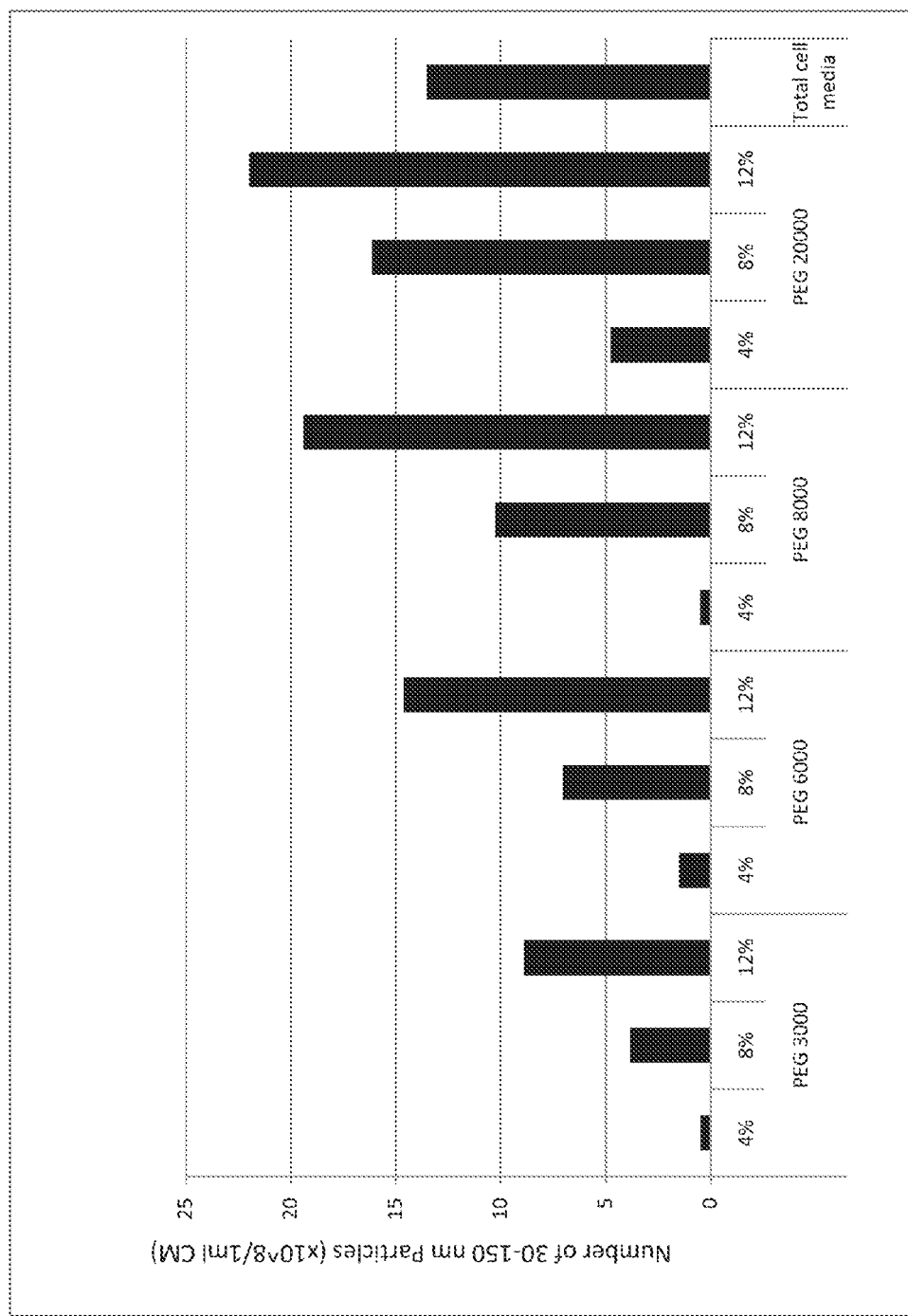
FIG. 1 Shows the results of an analysis comparing PEG size and concentration with the efficiency of exosome recovery from conditioned cell media.

Disclosed herein are methods and compositions using volume-excluding polymers such as polyethylene glycol (PEG) to precipitate exosomes from biological samples. The precipitated exosomes can be isolated using low-speed centrifugation, filtration or other methods for separating precipitated material.

As used herein, exosomes are small secreted vesicles (typically about 30-150 nm) which may contain, or have present in their membrane, nucleic acid, protein, or other biomolecules and may serve as carriers of this cargo between diverse locations in a body or biological system. When concentrations of volume excluding polymers are used they are presented as % weight/volume (w/v) calculated using the formula: weight of solute (g)/volume of solution (mL)*100.

The term biological fluid, as used herein, means any fluid isolated or derived from an organism including prokaryotes, eukaryotes, bacteria, fungi, yeast, invertebrates, vertebrates, reptiles, fish, insects, plants and animals. Media taken from cultured cells ("conditioned media", cell media, cell culture media) may be a biological fluid.

The term biological tissue, as used herein, means a collection of cells from prokaryotes, eukaryotes, bacteria, fungi, yeast, invertebrates, vertebrates, reptiles, fish, insects, plants and animals. Cultured cells may be a biological tissue.

Exosomes may be isolated from a variety of biological sources including mammals such as mice, rats, guinea pigs, rabbits, dogs, cats, bovine, horses goats, sheep, primates or humans. Typically, exosomes are isolated from biological fluids such as serum, plasma, whole blood, urine, saliva, breast milk, tears, sweat, joint fluid, cerebrospinal fluid, semen, vaginal fluid, ascetic fluid and amniotic fluid. Exosomes may also be isolated from experimental samples such as media taken from cultured cells ("conditioned media", cell media, cell culture media).

Exosomes may also be isolated from tissue samples such as surgical samples, biopsy samples, tissues, feces, plant tissue, insect tissue, and cultured cells. When isolating exosomes from tissue sources it may be necessary to homogenize the tissue in order to obtain a single cell suspension followed by lysis of the cells to release the exosomes. When isolating exosomes from tissue samples it is important to select homoginazation and lysis procedures that do not result in disruption of the exosomes.

Exosomes may be isolated from freshly collected samples or from samples that have been stored frozen or refrigerated. Although not necessary, higher purity exosomes may be obtained if fluid samples are clarified before precipitation with a volume-excluding polymer, to remove any debris from the sample. Methods of clarification include centrifugation, ultracentrifugation, filtration or ultrafiltration.

Precipitation of exosomes from the sample may be accomplished using a water-soluable volume excluding polymer. Examples of suitable polymers include polyethylene glycol (PEG), dextrans and derivatives such as dextran sulfate, dextran acetate, and hydrophilic polymers such as polyvinyl alcohol, polyvinyl acetate and polyvinyl sulfate.

Suitable volume-excluding polymers typically have a molecular weight between 1000 and 1,000,000 daltons. Polymers with higher molecular weights may be too viscous. In general, when higher concentrations of exosomes are present in a sample, lower molecular weight polymers may be used.

Volume-excluding polymers may be used at a final concentration of from 1% to 90% (w/v) upon mixing with the sample. For example, when one volume of 40% (w/v) polymer solution is mixed with equal volume of the biological fluid—the resulting polymer concentration in the sample is 20%. Higher concentrations of the volume-excluding polymers are useful when the concentration of the exosomes in the sample is low.

A variety of buffers commonly used for biological samples may be used for incubation of the exosome sample with the volume-excluding polymer including phosphate, acetate, citrate and TRIS buffers. The pH of the buffer may be any pH that is compatible with the sample, but a typical range is from 6 to 8. The buffer may have a pH from 4 to 10, 4 to 6, 4 to 8, 6 to 10, 6 to 8, or 8 to 10. The salt concentration can be any concentration that is compatible with the sample, but typically ranges from 10 mM to 500 mM. The salt concentration may be 10 mM to 500 mM, 10 mM to 50 mM, 10 mM to 100 mM, 10 mM to 200 mM, 10 mM to 300 mM, 10 mM to 400 mM, 50 mM to 500 mM, 100 mM to 500 mM, 200 mM to 500 mM, 300 mM to 500 mM, or 400 mM to 500 mM.

Incubation of the sample with the volume-excluding polymer may be performed at room temperature (about 20° C.) or higher temperature, but precipitation of the exosomes will generally occur more quickly and completely if the incubation is performed at a reduced temperature such as 4° C. Incubation may be performed at 1° C. to 40° C., 1° C. to 4° C., 4° C. to 10° C., 10° C. to 20° C., 20° C. to 30° C., or 30° C. to 40° C.

The time of incubation of the sample with the volume-excluding polymer may be any, typically in the range 1 sec-24 hours, more typically in the range 5 min-14 hours. The incubation time may be 1 sec-24 hours, 1 minute-24 hours, 5 minutes-24 hours, 10 minutes-24 hours, 20 minutes-24 hours, 30 minutes-24 hours, 1 hour-24 hours, 6 hours-24 hours, 12 hours-24 hours, 1 minute-12 hours, 1 minute-6 hours, or 1 minute-4 hours. The incubation time is influenced by, among other factors, the concentration of the volume-excluding polymer, the molecular weight of the volume-excluding polymer, the temperature of incubation and the concentration of exosomes and other components in the sample. High concentrations of high molecular weight volume-excluding polymers in general will precipitate exosomes more quickly. Samples with low concentrations of exosomes may require longer incubation times for efficient precipitation of exosomes.

After completion of the incubation of the sample with the volume-excluding polymer the precipitated exosomes may be isolated by centrifugation, ultracentrifugation, filtration or ultrafiltration. Exosomes may be further fractionated using conventional methods such as ultracentrifugation with or without the use of a density gradient to obtain higher purity. Sub-populations of exosomes may also be isolated by using other properties of the exosome such as the presence of surface markers. Surface markers which may be used for fraction of exosomes include but are not limited to tumor markers and MHC class II markers. MHC class II markers which have been associated with exosomes include HLA DP, DQ and DR haplotypes. Other surface markers associated with exosomes include CD9, CD81, CD63 and CD82 (Thery et al. Nat. Rev. Immunol. 2 (2002) 569-579; Valadi et al. Nat. Cell. Biol. 9 (2007) 654-659).

As an example, exosomes having CD63 on their surface may be isolated using antibody coated magnetic particles. Dynabeads® are super-paramagnetic polystyrene beads which may be conjugated with anti-human CD63 antibody, either directly to the bead surface or via a secondary linker (e.g. anti-mouse IgG). The beads may be between 1 and 4.5 μm in diameter.

The antibody coated Dynabeads® may be added to an exosome sample prepared using a volume-excluding polymer and incubated at 2-8° C. or at room temperature from 5 minutes to overnight. Dynabeads® with bound exosomes may then be collected using a magnet. The isolated, bead bound exosomes may then be resuspended in an appropriate buffer such as phosphate buffered saline and used for downstream analysis (qRT-PCR, sequencing, Westerns, flow cytometry etc.). Similar protocols may be used for any other surface marker for which an antibody or other specific ligand is available. Indirect binding methods such as those using biotin-avidin may also be used.

Once an isolated exosome sample has been prepared, the contents of the exosome may be extracted for study and characterization. Biological material which may be extracted from exosomes includes proteins, peptides, RNA and DNA, lipids. For example the mirVana™ PARIS Kit (AM1556, Life Technologies) may be used to recover native protein and RNA species, including small RNAs such as miRNA, snRNA, and snoRNA, from exosomes.

Total RNA may be extracted using acid-phenol:chloroform extraction. RNA may then be purified using a glass-fiber filter under conditions that recover small-RNA containing total RNA, or that separate small RNA species less than 200 nucleotides in length from longer RNA species such as mRNA. Because the RNA is eluted in a small volume, no alcohol precipitation step may be required for isolation of the RNA.

Kits may comprise one or more vessels containing one or more volume-excluding polymers, one or more buffers or one more solutions for performing density gradient centrifugation of exosomes. The kit may further comprise a filtration device for separating exosomes by their size. The kit may also comprise one or more antibodies or other ligands which bind to a protein or other antigen exposed on the surface of the exosome and one or more solid supports which bind directly or indirectly to the exosomes.

Preparation of Polyethylene Glycol (PEG) Stock Solutions

For preparation of 50 mL stock of 40% (w/v) PEG8000 in water, 20 grams of PEG8000 powder (Sigma) may be weighed and transferred into a 50 mL conical tube (Ambion). 20 mLs of nuclease-free water (Ambion) may then be added, and the tube placed into a Sarstedt M200 mixer (Germany) and dissolved for 1 hour or until the solution becomes clear. The contents of the tube may then be transferred into a graduated cylinder and water added to bring the final volume to 50 mL. The contents of the graduated cylinder may then be transferred back into the conical tube, and mixed for another 10 min to ensure a homogenous 40% PEG solution. Solutions containing 10-50% PEG3000-PEG20,000, with or without PBS or other buffer or NaCl, may be prepared in a similar fashion. PEG solution stocks may be stored at room temperature or 4° C. long term. Antibacterial agents such as sodium azide may be added to PEG stock solutions to prevent bacterial growth.

Extraction of Exosomes from Blood Serum

Blood serum samples are removed from storage and placed on ice. When serum is frozen it may be thawed slowly at room temperature in lukewarm water until the sample is completely liquid. Samples may be stored on ice until needed. The serum samples may be centrifuged at 2,000×g for 30 minutes to remove cell debris. Next, the supernatant containing the cell-free serum may be transferred to a fresh container and held on ice until precipitation.

For exosome precipitation, 100 μL to 1 mL (or other preferred volume) of cell-free serum may be transferred to a new tube and combined with the desired volume of PEG precipitation reagent.

For example, to achieve a 10% final concentration of PEG8000, 33.3 μL of 40% (w/v) PEG stock may be added to 100 μl of serum. The serum/reagent mixture may then be mixed well either by vortexing or pipetting up and down until there is a homogenous solution. (Solution may have a cloudy appearance). The samples may then be incubated at 4° C. for 5 minutes to 2 h. After incubation, the samples may be centrifuged at room temperature or 4° C. at 2,000×g to 10,000×g for 5-20 min. The supernatant is aspirated and discarded. Exosomes will be contained in the pellet at the bottom of the tube. The pellet may be resuspended in a convenient volume of phosphate bufferd saline (PBS) buffer, e.g. 50 μL for 100 μL serum input. The pellet in certain cases may be difficult to resuspend so a pipet tip may be used to completely resuspend it in the solution. Alternatively, the pellets may be incubated for 30 minutes at 37° C. then vortexed. Once the pellet has been resuspended, it may be stored at 4° C. short term or at −20° C. long term. Solutions containing PEG3000 to PEG20,000, at 3-15% final concentration (when mixed with serum sample), with or without PBS buffer or NaCl, may be used in a similar fashion, with serum input typically ranging from several microliters to several milliliters.

Quantification and Sizing of Exosomes with Nanosight LM10 Instrument.

Exosomes purified from blood serum and cell media by PEG precipitation may be quantified and sized using a Nanosight LM10 instrument (Nanosight, UK), following the manufacturer's protocol. This instrument uses a laser light source to illuminate nano-scale particles introduced to a viewing unit. Particles appear individually as point-scatterers moving under Brownian motion. The image analysis NTA software allows the user to automatically track and size nanoparticles on an individual basis.

Typically, exosome samples may be diluted 10-1000× with PBS buffer in order to achieve the nanoparticle concentration range suitable for analysis by Nanosight. A 300-500 uL volume may then be analyzed as recommended in the manufacturer's protocol.

EXAMPLES

Example 1

Evaluation of PEGs of Different Length and Percent for Capability to Isolate Exosomes from Cell Media Polyethylene glycol (PEG) of different length and percent were evaluated for capability to isolate exosomes from cell culture media (CM, cell media, conditioned media). HeLa cells were grown in a $CO_2$ incubator under normal conditions, in the recommended cell media containing 10% FBS, until ~80% confluency was reached. Then, cells were washed with PBS, and media was replaced with fresh media with 10% exosome-depleted FBS (exosomes were removed from FBS by ultracentrifugation) and cells were allowed to grow for another 12 h. The cell media was then harvested and centrifuged at 2,000×g for 30 minutes to remove cell debris. Next, the supernatant containing the cell-free cell media was transferred to a fresh container and held at room temperature until precipitation. For exosome precipitation, 1 mL of cell media was combined with the PEG precipitation reagent.

In this experiment, polyethylene glycol (PEG) of four different lengths was evaluated: PEG 3000, PEG 6000, PEG 8000, PEG 20000; all at three percentages: 4%, 8%, 12%. NaCl solution was added to the final concentration of 300 mM.

The samples (PEG+cell media) were incubated at 4° C. for 14 h, then the samples were spun down at 10,000 g for 1 h. The supernatant was discarded, and the exosome pellet was resuspended in PBS and number of exosomes was quantified on a Nanosight LM10 instrument. The number of exosomes in the samples (30-150 nm size range) was compared to the number of nanoparticles in the same size range in the original total cell media sample to analyze efficiency of recovery.

Results are shown in FIG. 1. As can be seen, all PEGs were capable of isolating exosomes from the cell media samples. The longer PEGs, 6000-20000 performed best, while PEG3000 was somewhat less efficient. A higher percentage of PEG was beneficial. At 8-12% PEG, recovery of exosomes was very efficient. At a 4% PEG concentration (for all PEGs 3000-20000) exosome recovery from cell media was less efficient. Note that at the optimal conditions (eg PEG 8000 12%) recovery of the exosomes was quantitative, as seen from comparison with the total cell media sample. In a similar fashion, exosomes can be isolated from the media from any other cell type, grown to any confluency, in a wide range of sample volume inputs.

Example 2

Investigation of Salt Effects on the Efficiency of PEG-Mediated Isolation of Exosomes from Cell Media Effects of salt and buffer on the efficiency of PEG-mediated isolation of exosomes from cell media were investigated. HeLa cells were grown in a $CO_2$ incubator under normal conditions, in the recommended cell media containing 10% FBS, until reaching about 80% confluency. Then, fresh media was added, without FBS, and cells were allowed to grow for another 12 h. The cell media was then harvested and centrifuged at 2,000×g for 30 minutes to remove cell debris. Next, the supernatant containing the cell-free cell media was transferred to a fresh container and held at room temperature until precipitation. For exosome precipitation, 1 mL or 5 mL of cell media was combined with the PEG precipitation reagent.

In this experiment, 8% PEG6000 was utilized, at several NaCl or PBS concentrations. The samples (PEG+cell media) were incubated at 4° C. for 14 h, then the samples were spun down at 10,000×g for 1 h. The supernatant was discarded, and the exosome pellet was resuspended in PBS and the number of exosomes was quantified on a Nanosight LM10 instrument. The number of exosomes in the samples (30-150 nm size range) was compared to the number of nanoparticles in the same size range in the original total cell media sample.

Figure 2:
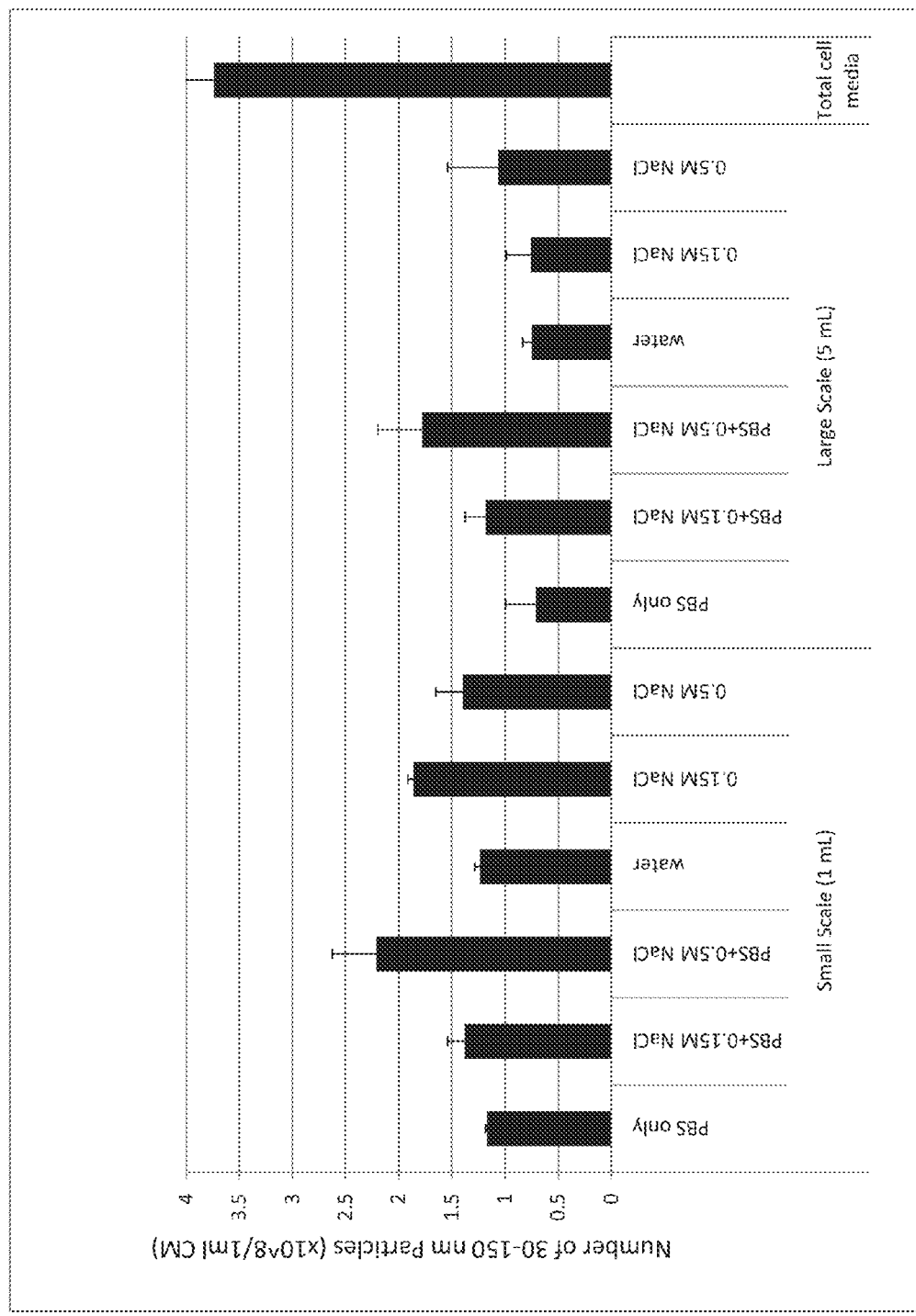
FIG. 2 Shows a comparison of different salt and buffer concentrations with the efficiency of exosome recovery from conditioned cell media.

Results are shown in FIG. 2. As can be seen, exosome isolation worked well at all conditions tested: PBS buffer only (no extra salt); PBS+0.15 M NaCl; PBS+0.5 M NaCl; water (no buffer; all buffering components and salts coming from cell media only); 0.15 M NaCl; 0.5 M NaCl; small scale (1 ml cell media input) and larger scale (5 mL cell media input).

Note that in this experiment cells were grown for the last 12 h prior to harvesting in media without FBS—to ensure high purity of exosomes. This results in a lower number of exosomes compared to cells grown in the presence of 10% exosome-depleted FBS (or 10% whole FBS). Lower numbers of exosomes in the original sample translates into a lower efficacy of isolation.

Example 3

Comparison of PEG-Mediated Isolation of Exosomes with Ultracentrifugation Protocol on Cell Media for Three Cell Types PEG-mediated isolation of exosomes was compared with ultracentrifugation protocol on cell media for three different cell types. HeLa, THP-1, Jurkat cells were grown in the $CO_2$ incubator under the normal conditions, in the recommended cell media containing 10% FBS, until about 80% confluency. Then, media was replaced with fresh media with 10% exosome-depleted FBS, and cells were allowed to grow for another 12 h. The cell media was then harvested and centrifuged at 2,000×g for 30 minutes to remove cell debris. Next, the supernatant containing the cell-free cell media was transferred to a fresh container and held at room temperature until precipitation. For exosome precipitation, 1 mL of cell media was combined with the PEG precipitation reagent.

In this experiment, 8% PEG6000 was utilized. The samples (PEG+cell media) were incubated at 4° C. for 14 h, then the samples were spun down at 10,000 g for 1 h. The supernatant was discarded, and the exosome pellet was resuspended in PBS and the number of exosomes was quantified on a Nanosight LM10 instrument. The number of exosomes in the samples (30-150 nm size range) was compared to the number of nanoparticles in the same size range in the original total cell media sample.

Figure 3:
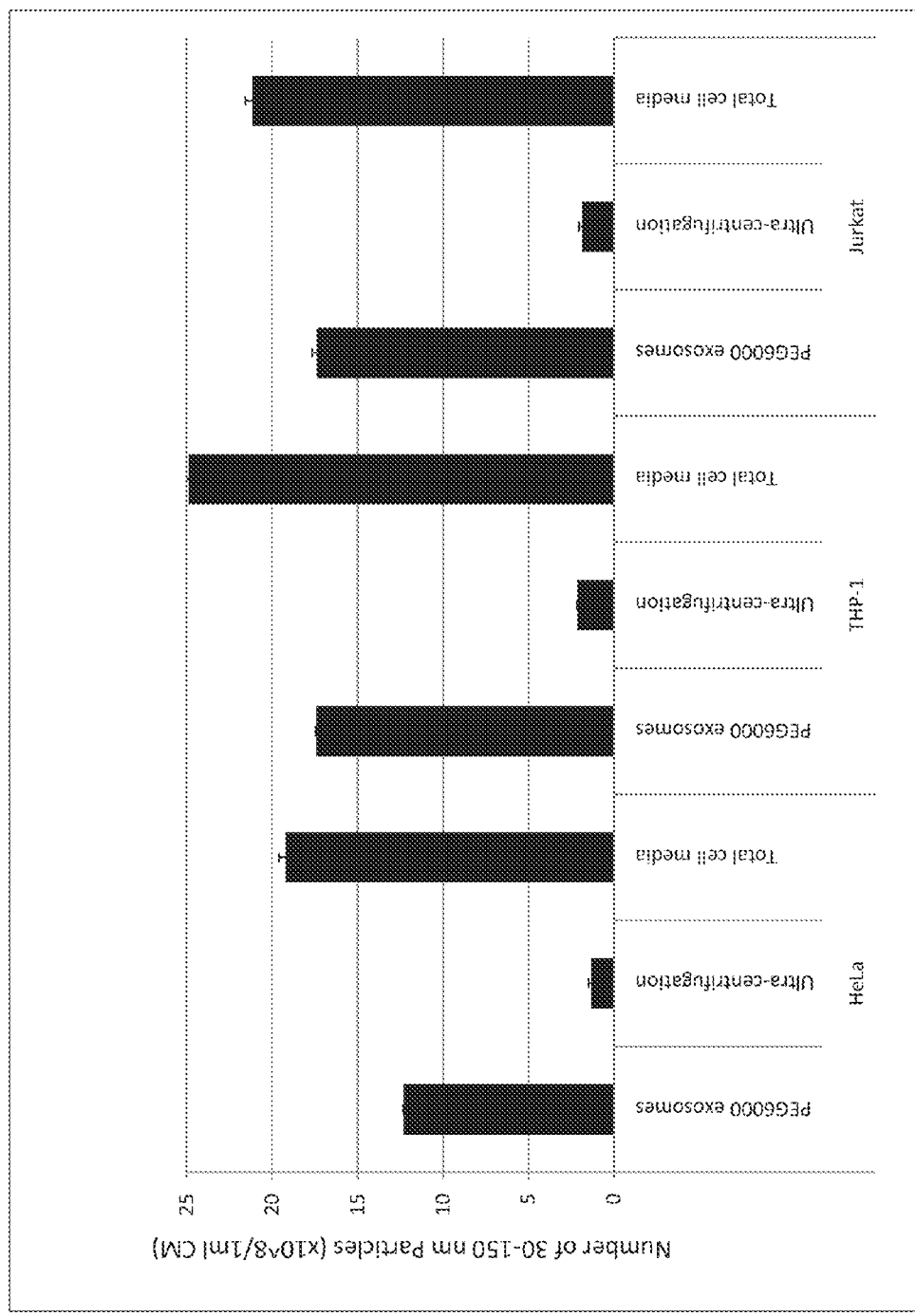
FIG. 3 Shows a comparison of PEG-mediated exosome isolation from three cell types with isolation of exosomes using the ultracentrifugation protocol.

Results are shown in FIG. 3. As can be seen, for all three types of cells, with PEG6000 used at final concentration of 8%, extremely efficient isolation of exosomes was achieved. Ultracentrifugation, currently the "gold standard" procedure for isolation of exosomes, results in significantly lower number of exosomes isolated from the same volume of cell media. Ultracentrifugation is also a very lengthy multi-step procedure requiring special instrumentation and training. PEG enables very fast and efficient isolation of exosomes from cell culture media, the protocol is robust and superior to ultracentrifugation in terms of the yield of exosomes obtained.

Figure 4:
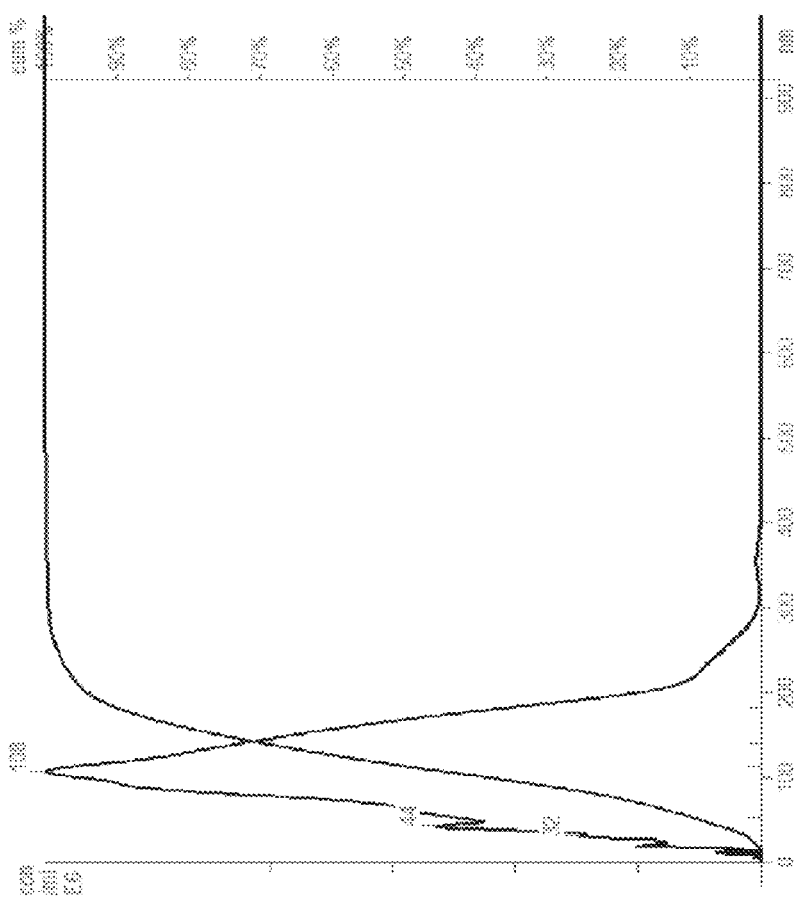
FIG. 4 Shows analysis of an exosome preparation isolated from HeLa cells. The X axis depicts the size distribution of the detected nanoparticles (in nanometers). The Y axis depicts the concentration of nanoparticles per mL of sample ($\times 10^6$).

The representative analysis of the exosome sample derived from the HeLa cell media is shown in FIG. 4. Exosomes isolated from 5 mL of HeLa cell media by 12% PEG6000 were resuspended in 200 µL of PBS, diluted 10 fold and analyzed using a Nanosight LM10 instrument. The X axis depicts the size distribution of the detected nanoparticles (in nanometers). The Y axis depicts the concentration of nanoparticles per mL of sample ($\times 10^6$). As can be seen, the majority of microvesicles isolated by PEG precipitation are in the size range typical for exosomes: 30-150 nm.

Example 4

Evaluation of PEGs of Different Length and Percent for Capability to Isolate Exosomes from Blood Serum Polyethylene glycol (PEG) of different length and percent were evaluated for capability to isolate exosomes from the blood serum.

The human blood serum samples were removed from storage and placed on ice. When serum was frozen, it was thawed slowly at room temperature in lukewarm water until the sample was completely liquid. Samples were stored on ice until needed. The serum samples were first centrifuged at 2,000×g for 30 minutes to remove cell debris. Next, the supernatant containing the cell-free serum was transferred to a fresh container and held on ice until precipitation.

For exosome precipitation, 100 µL of cell-free serum was transferred to a new tube and combined with the PEG precipitation reagent.

In this experiment, polyethylene glycol (PEG) of four different lengths was evaluated: PEG 3000, PEG 6000, PEG 8000, PEG 20000; all at two percentages: 8% and 15% (final PEG percent, upon mixing with the sample).

The samples (PEG+serum) were incubated at 4° C. for 1 h, then the samples were spun down at 10,000 g for 20 min. The supernatant was discarded, and the exosome pellet was resuspended in PBS and the number of exosomes was quantified on a Nanosight LM10 instrument. The number of exosomes in the samples (30-150 nm size range) was compared to the number of nanoparticles in the same size range in the original total serum sample to analyze the efficiency of recovery.

Figure 5:
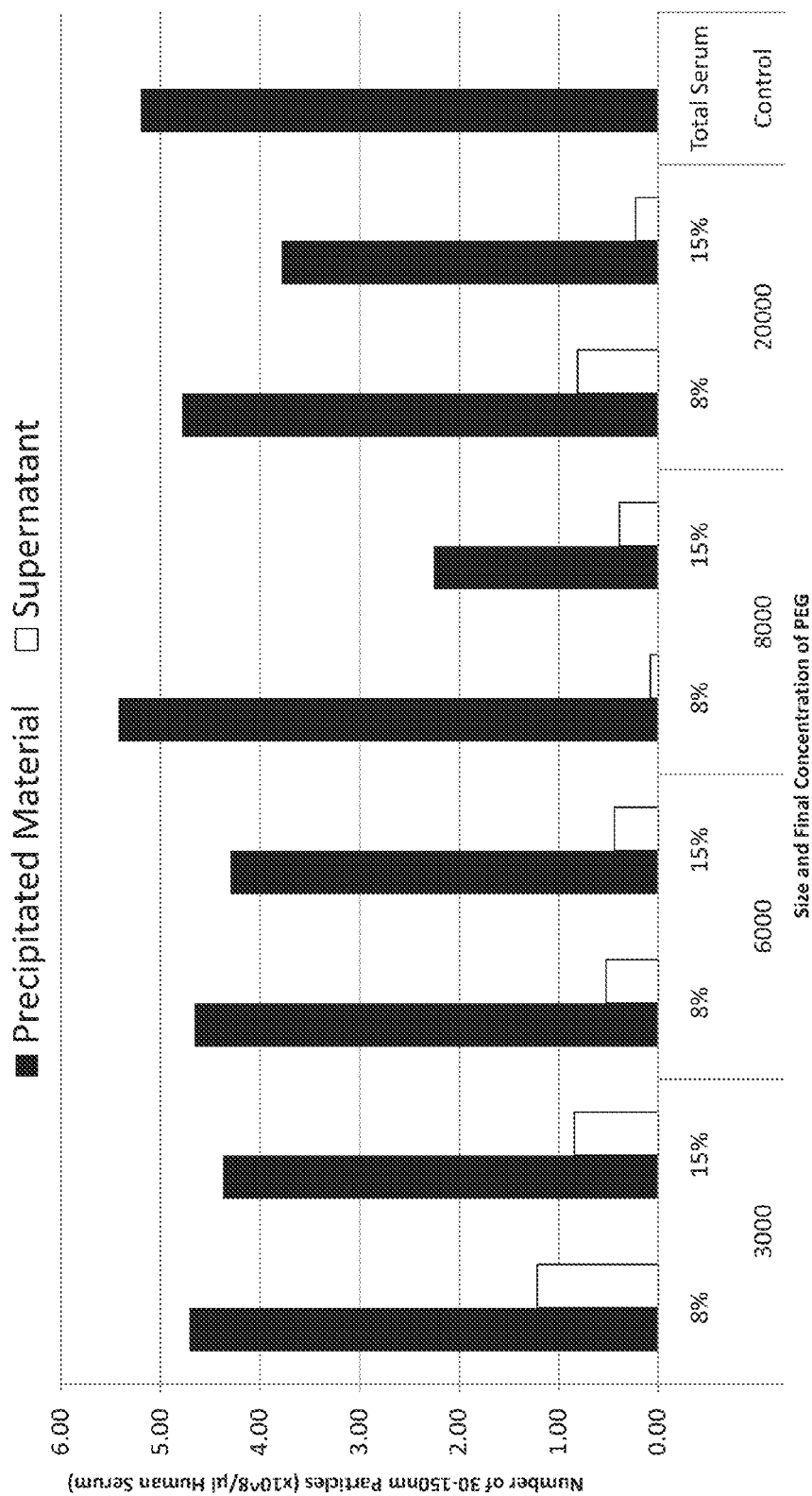
FIG. 5 Shows the results of an analysis comparing PEG size and concentration with the efficiency of exosome recovery from blood serum.

Results are shown in FIG. 5. As can be seen, all PEGs 3000-20000 were capable of isolating exosomes from the serum samples with about similar efficiency. Concentrations of PEG of 8% and 15% produced very similar results. Note that at the optimal conditions (eg PEG 6000 8%) recovery of the exosomes was quantitative as seen from comparison with the total serum sample. On the practical side, PEG 20000 is significantly more viscous and hard to pipet compared to shorter PEG 3000-8000. Also, PEG stock solutions 20-30% (weight/volume) are easier to work with compared to stock solutions of higher concentration (40-60% w/v) that are very viscous and hard to handle.

Example 5

Investigation of PEG6000 of Different Percent for Isolation of Exosomes from Blood Serum PEG6000 of different percent was investigated for efficiency of isolation of exosomes from blood serum. The human blood serum samples were removed from storage and placed on ice. When serum was frozen it was thawed slowly at room temperature in lukewarm water until sample was completely liquid. Samples were stored on ice until needed. The serum samples were first centrifuged at 2,000×g for 30 minutes to remove cell debris. Next, the supernatant containing the cell-free serum was transferred to a fresh container and hold on ice until precipitation.

For exosome precipitation, 100 µL of cell-free serum was transferred to a new tube and combined with the PEG precipitation reagent.

In this experiment, polyethylene glycol PEG 6000 was used, at six percentages: 3%, 4%, 5%, 6%, 7%, 8% (final PEG percent, upon mixing with the biological samples).

The samples (PEG+serum) were incubated at 4° C. for 1 h, then the samples were spun down at 10,000 g for 20 min. The supernatant was discarded, and the exosome pellet was resuspended in PBS and number of exosomes was quantified on a Nanosight LM10 instrument. The number of exosomes in the samples (30-150 nm size range) was compared to the number of nanoparticles in the same size range in the original total serum sample to analyze efficiency of recovery.

Figure 6:
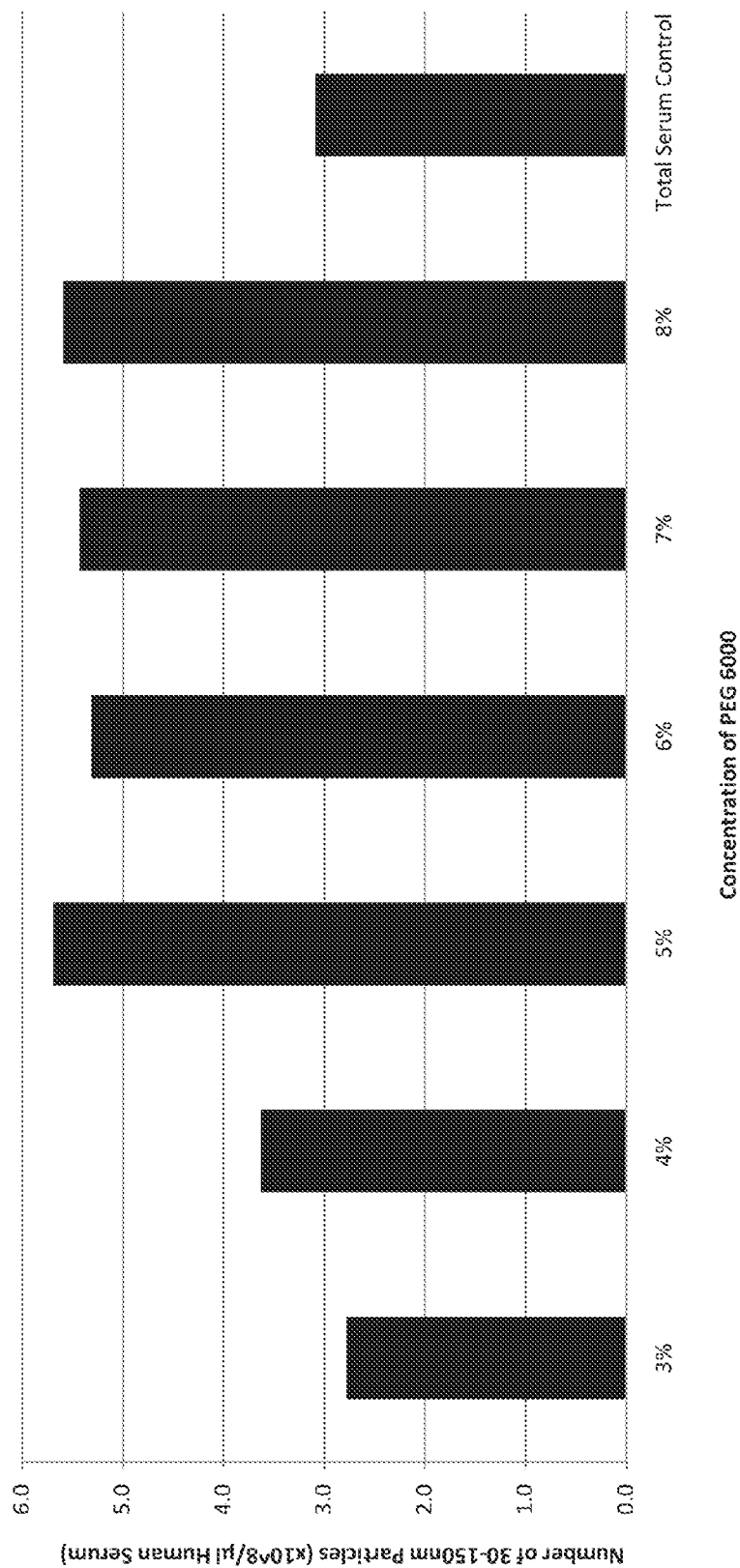
FIG. 6 Shows the comparison of PEG6000 of different concentrations for isolation of exosomes from blood serum.

Results are shown in FIG. 6. As can be seen, PEG6000 at all concentrations from 3%-8% was capable of isolating exosomes from serum samples with high efficiency. PEG at 3% and 4% was somewhat less efficient compared to PEG at 5-8%. Recovery of exosomes was essentially quantitative starting from 4% PEG6000 as seen from comparison with the total serum sample. In a similar fashion, exosomes can be isolated from any other type of body or biological fluid, in the wide range of sample volume inputs.

Example 6

Comparison of Small Scale Vs Large Scale Exosome Isolation, and Sample to Sample Variation Comparison of small scale vs large scale exosome isolation from blood serum was performed, and sample to sample variation was studied. Human blood serum samples were removed from storage and placed on ice. When serum was frozen, it was thawed slowly at room temperature in lukewarm water until sample was completely liquid. Samples were stored on ice until needed. Serum samples were first centrifuged at 2,000×g for 30 minutes to remove cell debris. Next, the supernatant containing the cell-free serum was transferred to a fresh container and held on ice until precipitation.

For exosome precipitation, 100 μL or 1 mL of cell-free blood serum was transferred to a new tube and combined with the PEG precipitation reagent.

In this experiment, 5% PEG 6000 was used. The samples (PEG+serum) were incubated at 4° C. for 1 h, then the samples were spun down at 10,000 g for 10 min. The supernatant was discarded, and the exosome pellet resuspended in PBS and the number of exosomes was quantified on a Nanosight LM10 instrument. The number of exosomes in the samples (30-150 nm size range) was compared to the number of nanoparticles in the same size range in the original total serum sample to analyze efficiency of recovery.

Figure 7:
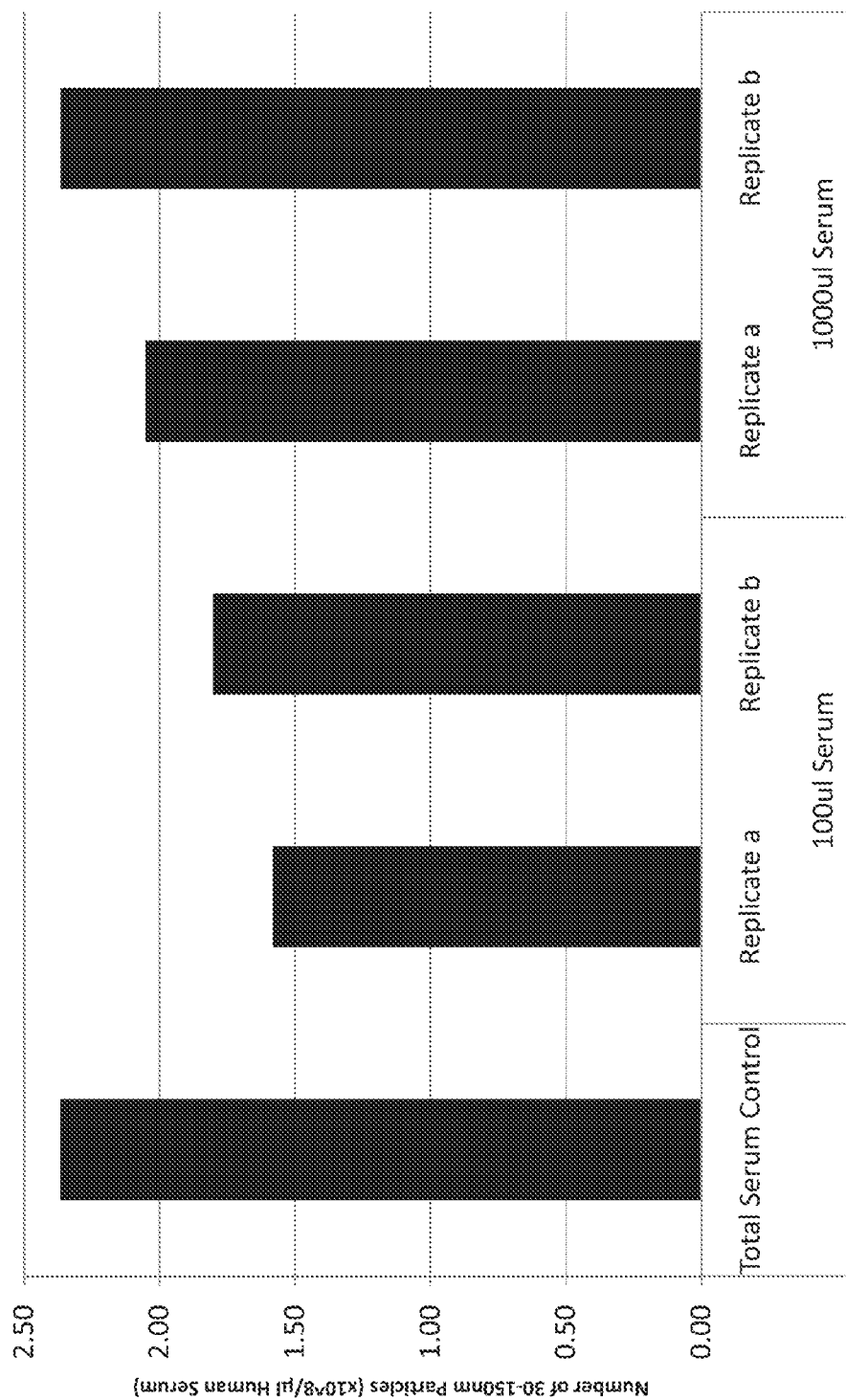
FIG. 7 Shows a comparison of small scale versus large scale exosome isolation from serum.

Results are shown in FIG. 7. As can be seen, 5% PEG6000 enabled efficient isolation of exosomes from the serum for both 100 μL sample input (small scale) as well as 1 mL input (large scale). In both cases, isolation efficiency is very high. This experiment was carried out in duplicate, and the variation between replicates was relatively small, indicating that the process of PEG-mediated exosomes isolation is robust. In a similar fashion, isolation of exosomes from other biological fluids can be performed, for any sample volume inputs (typically ranging from microliters to milliliters, but in certain cases up to liters—especially for cell culture media).

Example 7

Isolation of the Exosomal RNA Cargo and Analysis by qRT-PCR

Following exosomes isolation from serum by PEG6000 (6%, 8% or 10%), total exosomal RNA was extracted and qRT-PCR analysis was performed. The human blood serum samples were removed from storage and placed on ice. When serum was frozen it was thawed slowly at room temperature in lukewarm water until sample was completely liquid. Samples were stored on ice until needed. The serum samples were first centrifuged at 2,000×g for 30 minutes to remove cell debris. Next, the supernatant containing the cell-free serum was transferred to a fresh container and hold on ice until precipitation.

For exosome precipitation, 100 μL of cell-free serum was transferred to a new tube and combined with the PEG precipitation reagent. In this experiment, polyethylene glycol PEG 6000 was used, at three percentages: 6%, 8%, 10%. The samples (PEG+serum) were incubated at 4° C. for 1 h, then the samples were spun down at 10,000 g for 20 min. The supernatant was discarded, and the exosome pellet was resuspended in PBS. RNA was isolated using the miRVana™ PARIS (Life Technologies) serum protocol and then qRT-PCR analysis was performed for GAPDH mRNA and miR26a.

Figure 8:
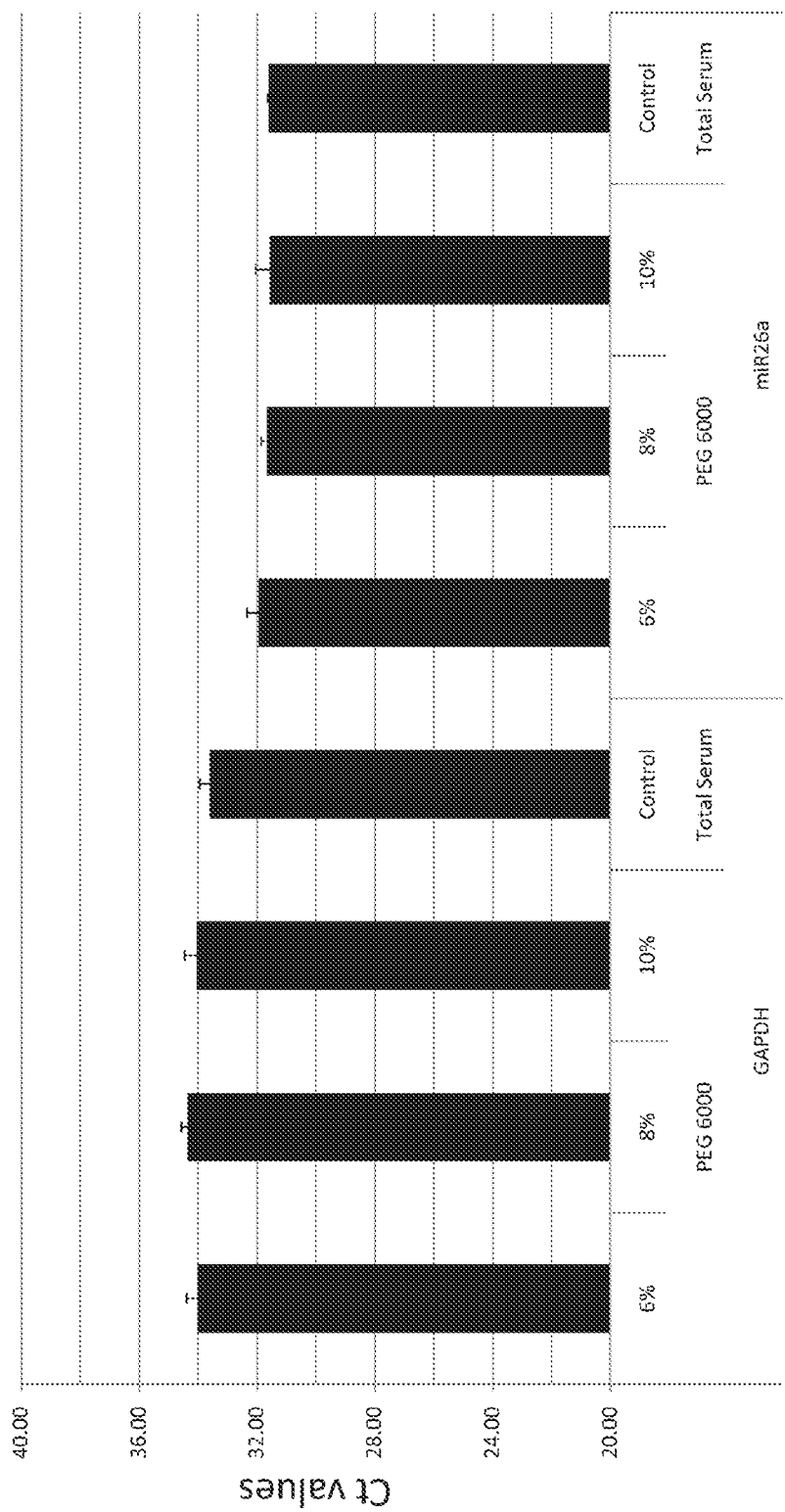
FIG. 8 Shows the analysis of exosomal RNA by qRT-PCR.

Results are shown in FIG. 8. PEG6000 at 6%-10% was capable of isolating exosomes from the serum samples with high efficiency as seen from comparison with the total serum sample. RNA isolation using the miRVana™ PARIS kit was successful. Both GAPDH and miR26a quantification by TaqMan® assays was robust and efficient.

Figure 9:
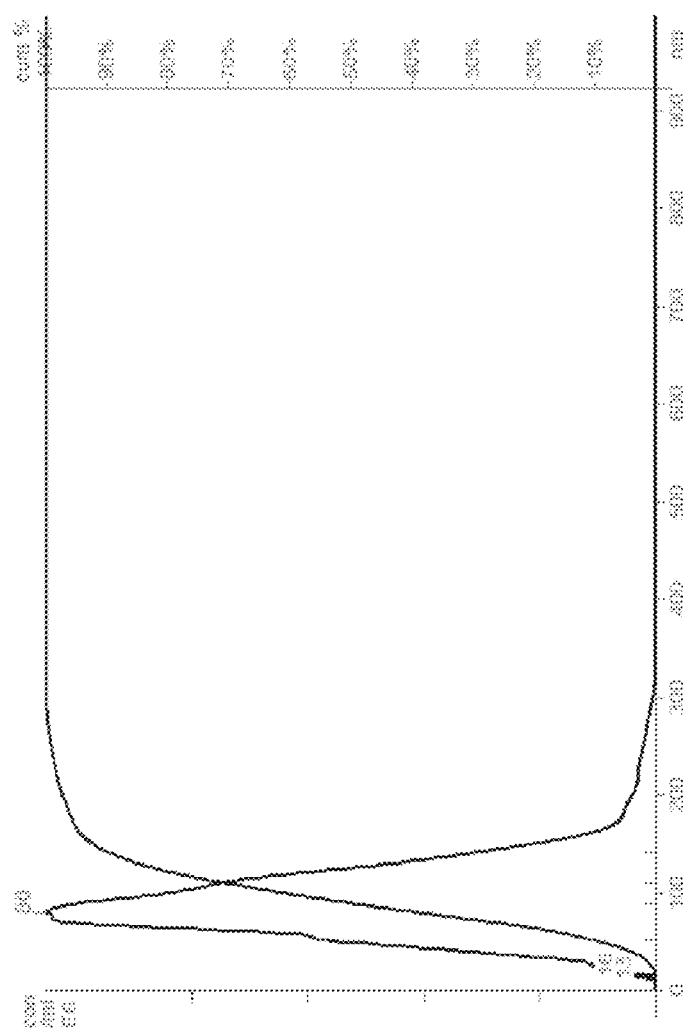
FIG. 9 Shows analysis of an exosome preparation isolated from human blood serum. The X axis depicts size distribution of the detected nanoparticles (in nanometers). The Y axis depicts concentration of nanoparticles per mL of sample ($\times 10^6$).

The representative analysis of the exosome sample derived from human blood serum is shown in FIG. 9. Exosomes isolated from 100 uL of serum by 8% PEG6000 were resuspended in 25 μL of PBS, diluted 1000 fold and analyzed using a Nanosight LM10 instrument. The X axis depicts size distribution of the detected nanoparticles (in nanometers). The Y axis depicts concentration of nanoparticles per mL of sample ($\times 10^6$). As can be seen, majority of microvesicles isolated by PEG precipitation are in the size range typical for exosomes: 30-150 nm.

Example 8

Electron Microscopy Analysis of Exosomes Isolated from Three Cell Lines with 10% PEG6000

Exosomes were isolated from Ramos, Sudhl4, SW480 and cell culture media. 5 mL cell media aliquots (after 30 min 2000 g centrifugation to remove cell debris) were combined with 2.5 mL (½ vol) of 30% (w/v) PEG6000 stock solution, resulting in 10% final PEG concentration. The samples (PEG6000+cell media) were mixed and incubated at 4° C. for ~14 h, then the samples were spun down at 10,000 g for 1 h. The supernatant was discarded, and the exosome pellet was used for downstream analysis by Electron Microscopy (EM)—in the unlabeled form, and also labeled with two types of antibodies conjugated to gold nanoparticles.

For immunolabelling, exosome loading was precipitated undiluted at room temperature for 15 min to grids. Next, blocking with 0.5% BSA was performed for 10 min. Labeling with anti-CD81 and anti-CD63 antibodies (the standard exosomal surface markers) was carried out for 30 min. Following washing steps, Prot A Au 10 nm were added and incubated for 15 min. After PBS and water wash steps, embedding in 0.3% Uranyl acetate in methyl cellulose was finally performed, followed by Electron Microscopy analysis.

Figure 10:
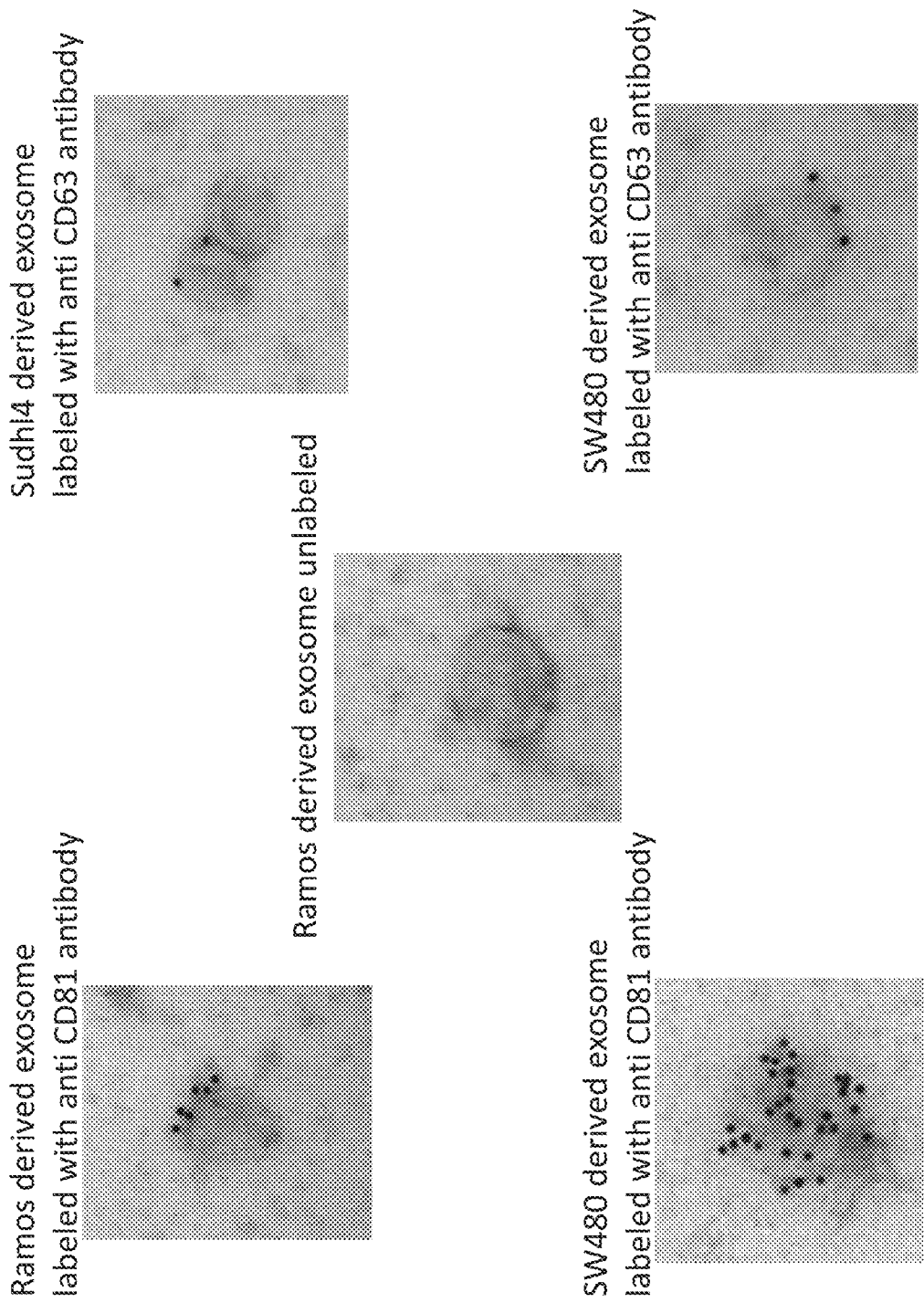
FIG. 10 Shows Electron Microscopy analysis of exosomes isolated from cell culture media with 10% PEG6000.

The results of analysis of immunolabeled, negative stain exosomes—recovered from the media of three cell lines with the PEG6000 reagent, are shown in FIG. 10. Ramos (unlabeled and labeled with anti-CD81 antibodies), Sudhl4 (labeled with anti-CD63 antibodies), SW480 (labeled with anti-CD63 and anti-CD81 antibodies) exosomes are shown. Exosomes are in the 100 nm range, and gold particles (attached to antibodies)—10 nm in size.

The exosomes recovered with 10% PEG6000 have typical appearance and size, and immunolabeling with anti-CD81 and anti-CD63 antibodies (which are well known exosomal markers)—clearly demonstrate that PEG6000 enabled isolation of clean population of high quality exosomes.

Example 9

Comparison of RNA and Protein Content of Exosomes Isolated from HeLa Cell Culture Media with 10% PEG6000 Versus Ultracentrifugation Protocol Exosomes were isolated from HeLa cell culture media: 1 mL cell media aliquots (after 30 min 2000 g centrifugation to remove cell debris) were combined with 0.5 mL of 30% PEG6000 stock solution (w/v), resulting in 10% final PEG concentration. The samples (PEG6000+cell media) were carefully mixed and incubated at 4° C. for ~14 h, then the samples were spun down at 10,000 g for 1 h. The supernatant was discarded, the exosome pellet resuspended in PBS buffer and analyzed for presence of typical RNA and protein markers. Exosomes were also recovered from the same starting HeLa cell culture media samples, following the standard ultracentrifugation protocol with sucrose gradient (C. Thery et al., Current Protocols in Cell Biol (2006) 3.22.1-3.22.29)—for comparison purposes.

First, presence of well known CD63 exosomal marker in the samples obtained with PEG6000 and ultracentrifugation was analyzed by Western Blots. Exosome samples were mixed with 2× non-reducing Tris-glycine SDS sample buffer (Novex®), then heated at 75° C. for 5 min and loaded onto a 1.5 mm×15 well 4-20% Tris-Glycine gel (Novex®). Benchmark prestained protein ladder (Invitrogen) was added to one well as a control to monitor the molecular weight of the protein samples. The gel was run under denaturing conditions at 150 V for 1.5 h then transferred to a membrane using the iBlot instrument (Life Technologies). After transfer, the membranes were processed on the BenchPro® 4100 (Life Technologies) with CD63 antibody diluted 100× to 20 ml (Abcam). The WesternBreeze Chemiluminescence kit was utilized on the next step, membranes were exposed to X-ray film for 1-10 min and the film was analyzed.

Figure 11:
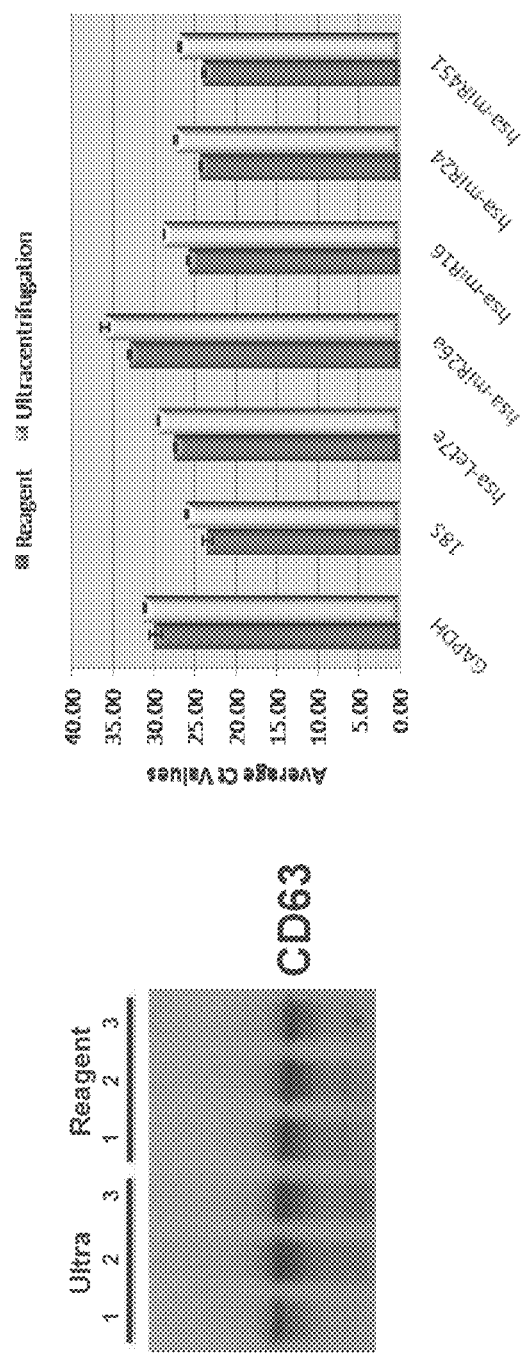
FIG. 11 Shows Western blot and qRT-PCR analysis for exosomes derived from HeLa cell media with 10% PEG6000.

The results are shown in FIG. 11 (left panel), in triplicate. Exosomes isolated with ultracentrifugation protocol and 10% PEG6000 were both positive for CD63 marker, and the differences were marginal if any. This indicates that polyethyleneglycol (PEG), of optimized length and percentage, allows recovery of high quality exosomes from the biological samples.

Next, RNA was isolated from the exosomes obtained with PEG6000 and ultracentrifugation, using mirVana™ Paris kit (Life Technologies), and the presence of certain RNA was analyzed by Reverse transcription and Quantitative real-time PCR (qRT-PCR). Reverse Transcription (RT) Master Mix was prepared for each sample using the TaqMan® MicroRNA Reverse Transcription Kit reagents and protocol (Applied Biosystems) with gene specific RT primers for the RNA targets. 10 µl of the RT Master Mix was added to corresponding wells in a 96-well plate, and 5 µl of each sample was added to the master mix. Plates were covered with adhesive (non-optical) cover and spun down to remove air bubbles then placed into a 9700 thermocycler and incubated as follows: 4° C. for 5 min; 16° C. for 30 min; 42° C. for 30 min; and 85° C. for 5 min. Reactions were kept at 4° C. until use.

qPCR master mixes were prepared for each of five microRNAs (let7e, miR26a, miR16, miR24 and miR451) and two mRNAs (GAPDH and 18S) by combining 5 µl of AB Universal PCR Master Mix II, 3.5 µl of nuclease-free water, and 0.5 µl of the 20× Taqman® Assay. After mixing, 8 µl of each master mix was placed into wells in a 384-well plate (enough for triplicate reactions for each isolation replicate). 2 µl of each RT reaction was added in triplicate to the master mix of each target and the plates were sealed with optical adhesive cover. Plate were spun down to remove air bubbles then placed into a 7900HT instrument and run using the following thermocycler protocol: 95° C. for 10 min; (95° C. for 15 s; 60° C. for 60 s) 40 cycles. Once the run was complete, automatic Ct analysis was performed with SDSv2.3 software and average and standard deviation was calculated for each set of isolations and qPCR reactions for each target.

The results are shown in FIG. 11 (right panel). The levels of five microRNAs (let7e, miR26a, miR16, miR24 and miR451) and two mRNAs (GAPDH and 18S) (earlier reported to be present in exosomes by Valadi et al. (Valadi et al., Nature Cell Biol 9 (2007) 654-659)), were quantified by qRT-PCR. Exosomes isolated with ultracentrifugation protocol and 10% PEG6000 both contain all these RNAs, in very similar levels (PEG recovers somewhat more material). This indicates that polyethyleneglycol, of optimized length and percentage, allows recovery of high quality exosomes from cell media samples.

Example 10

Comparison of RNA and Protein Content of Exosomes Isolated from Serum with 5% PEG6000 Versus Ultracentrifugation Protocol Exosomes were isolated from human serum: 100 µL serum (after 30 min 2000 g centrifugation to remove cell debris) were combined with 20 µL of 30% (w/v) PEG6000 stock solution, resulting in 5% final PEG concentration. The samples (PEG6000+serum) were carefully mixed and incubated at 4° C. for ~30 min, then the samples were spun down at 10,000 g for 10 min. The supernatant was discarded, the exosome pellet resuspended in PBS buffer and analyzed for presence of typical RNA and protein markers. Exosomes were also recovered from the same starting serum samples, following the standard ultracentrifugation protocol with sucrose gradient (C. Thery et al., Current Protocols in Cell Biol (2006) 3.22.1-3.22.29)—for comparison purposes.

Figure 12:
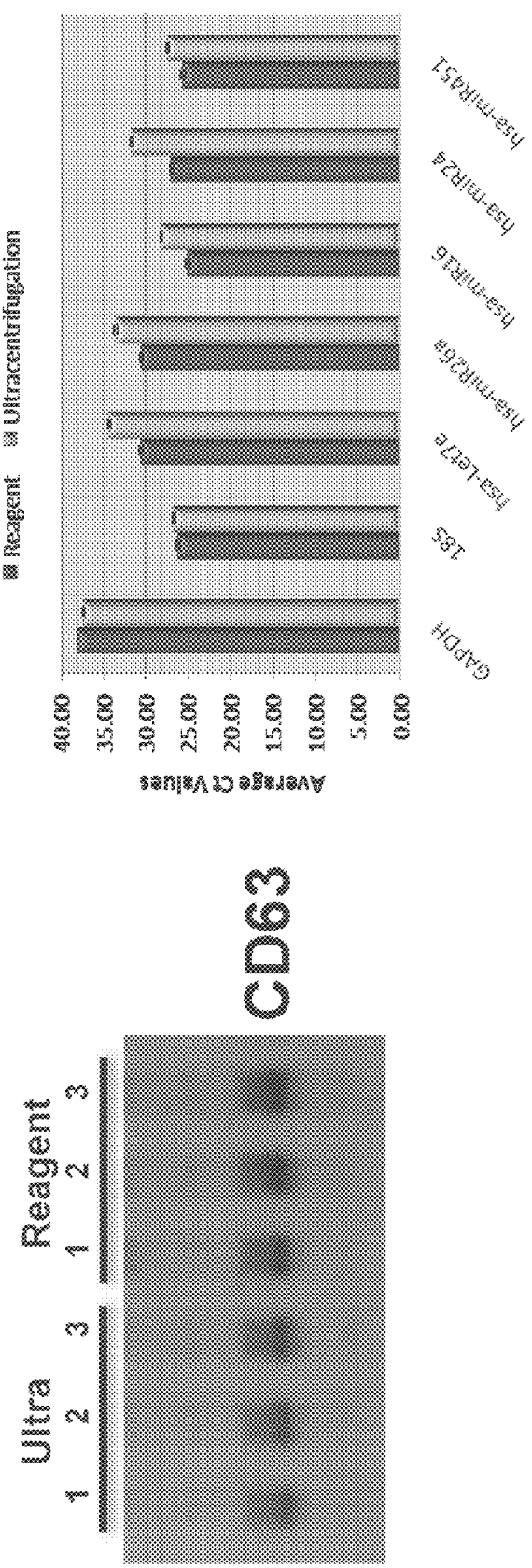
FIG. 12 Shows Western blot and qRT-PCR analysis for exosomes derived from serum with 5% PEG6000.

First, presence of well known CD63 exosomal marker in the samples obtained with PEG6000 and ultracentrifugation was analyzed by Western Blots. Protocol was the same as described in Example 9. The results are shown in FIG. 12 (left panel), in triplicate. Exosomes isolated with ultracentrifugation protocol and 5% PEG6000 were both positive for CD63 marker, and the differences were marginal if any. This indicates that polyethyleneglycol, of optimized length and percentage, allows recovery of high quality exosomes from the biological samples.

Next, RNA was isolated from the exosomes obtained with PEG6000 and ultracentrifugation, using mirVana™ Paris kit (Life Technologies), and the presence of certain RNA was analyzed by Reverse transcription and Quantitative real-time PCR (qRT-PCR). Reverse Transcription (RT) Protocol was the same as described in Example 9. The results are shown in FIG. 12 (right panel). The levels of five microRNAs (let7e, miR26a, miR16, miR24 and miR451) and two mRNAs (GAPDH and 18S) (earlier reported to be present in exosomes by Valadi et al. (Valadi et al., Nature Cell Biol 9 (2007) 654-659)), were quantified by qRT-PCR. Exosomes isolated with ultracentrifugation protocol and 5% PEG6000 both contain all these RNAs, in very similar levels (PEG recovers somewhat more material). This indicates that polyethyleneglycol, of optimized length and percentage, allows recovery of high quality exosomes from blood serum samples.

Example 11

Recovery of Exosomes from Urine with 10-20% PEG6000

Exosomes were isolated from human urine: 5 mL urine samples from three healthy donors (after 30 min 2000 g centrifugation to remove cell debris) were combined with PEG6000 stock solution, resulting in 10%, 12%, 15% and 20% final PEG concentration. The samples (PEG6000+urine) were carefully mixed and incubated at 4° C. for ~14 h, then the samples were spun down at 10,000 g for 1 h. The supernatant was discarded, and the exosome pellet was resuspended in PBS and the number of exosomes was quantified on a Nanosight LM10 instrument. The number of exosomes in the samples (30-150 nm size range) was compared to the number of nanoparticles in the same size range in the original whole urine sample and cell-free sample (whole urine, subjected to 30 min 2000 g centrifugation to remove cell debris)—to analyze the efficiency of recovery. The entire population of nanoparticles in the size range 0-2000 nm was tracked as well.

Figure 13:
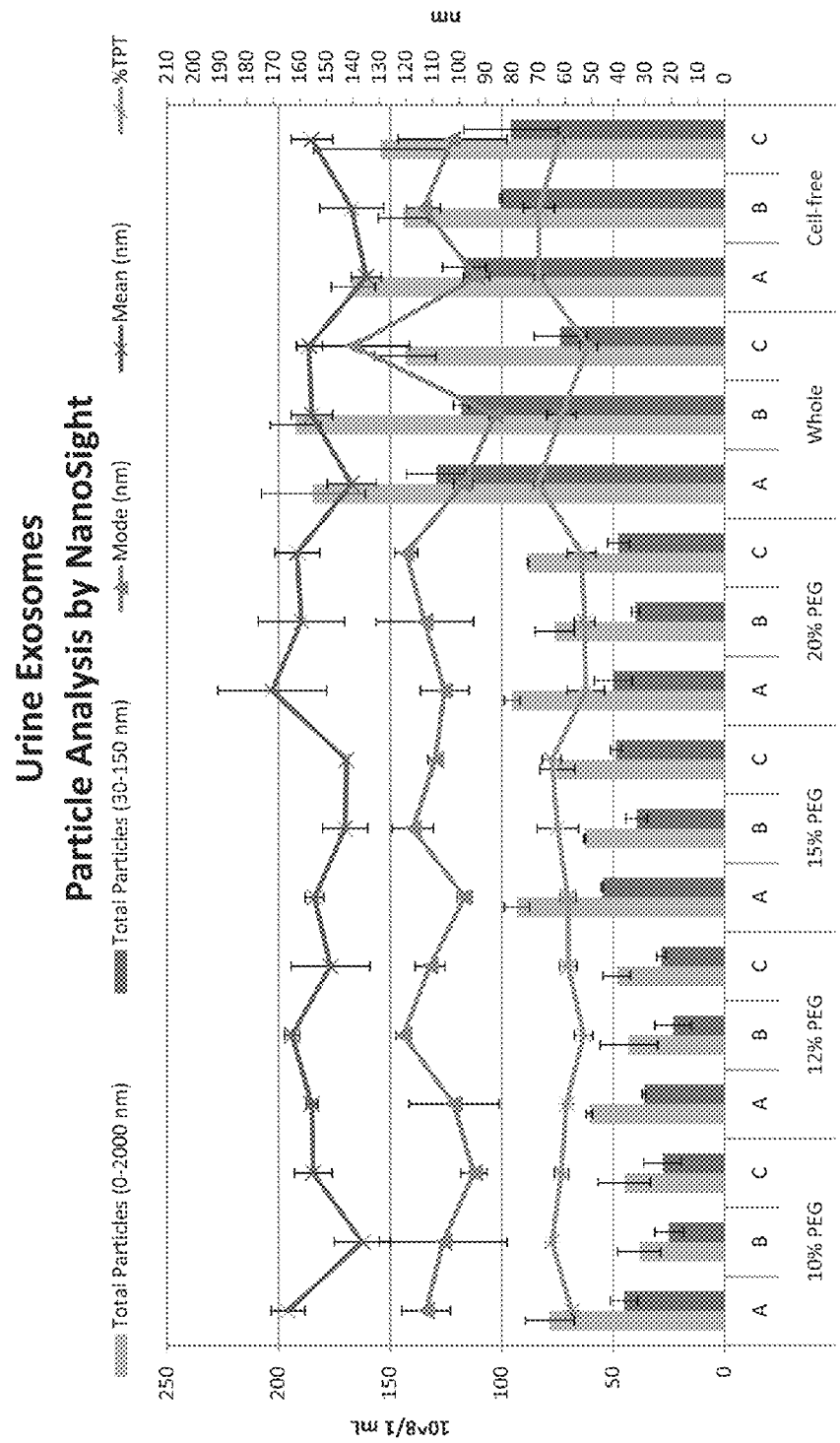
FIG. 13 Shows efficiency of exosomes recovery from urine with PEG6000 of different percentages.

The results are shown in FIG. 13. For all three donors (A, B, C) PEG6000 at concentrations 10-20% allows very efficient recovery of exosomes from urine. Higher PEG concentrations, in particular 15-20%, results in more efficient extraction.

Example 12

Recovery of Exosomes from Amniotic Fluid with 2-14% PEG6000

Exosomes were isolated from human amniotic fluid: 1 mL amniotic fluid samples (after 30 min 2000 g centrifugation to remove cell debris) were combined with PEG6000 stock solution, resulting in 2%, 4%, 6%, 8%, 10%, 12% and 14% final PEG concentration. The samples (PEG6000+amniotic fluid) were carefully mixed and incubated at 4° C. for ~14 h, then the samples were spun down at 10,000 g for 1 h. The supernatant was discarded, and the exosome pellet was resuspended in PBS and the number of exosomes was quantified on a Nanosight LM10 instrument. As always, following the manufacturer's protocol the concentrated samples were diluted to ensure the concentration range of nanoparticles is suitable for accurate analysis by Nanosight LM10 instrument. The number of exosomes in the samples (30-150 nm size range) was compared to the number of nanoparticles in the same size range in the original amniotic fluid sample (subjected to 30 min 2000 g centrifugation to remove cell debris)—to analyze the efficiency of recovery. The entire population of nanoparticles in the size range 0-2000 nm was tracked as well.

Figure 14:
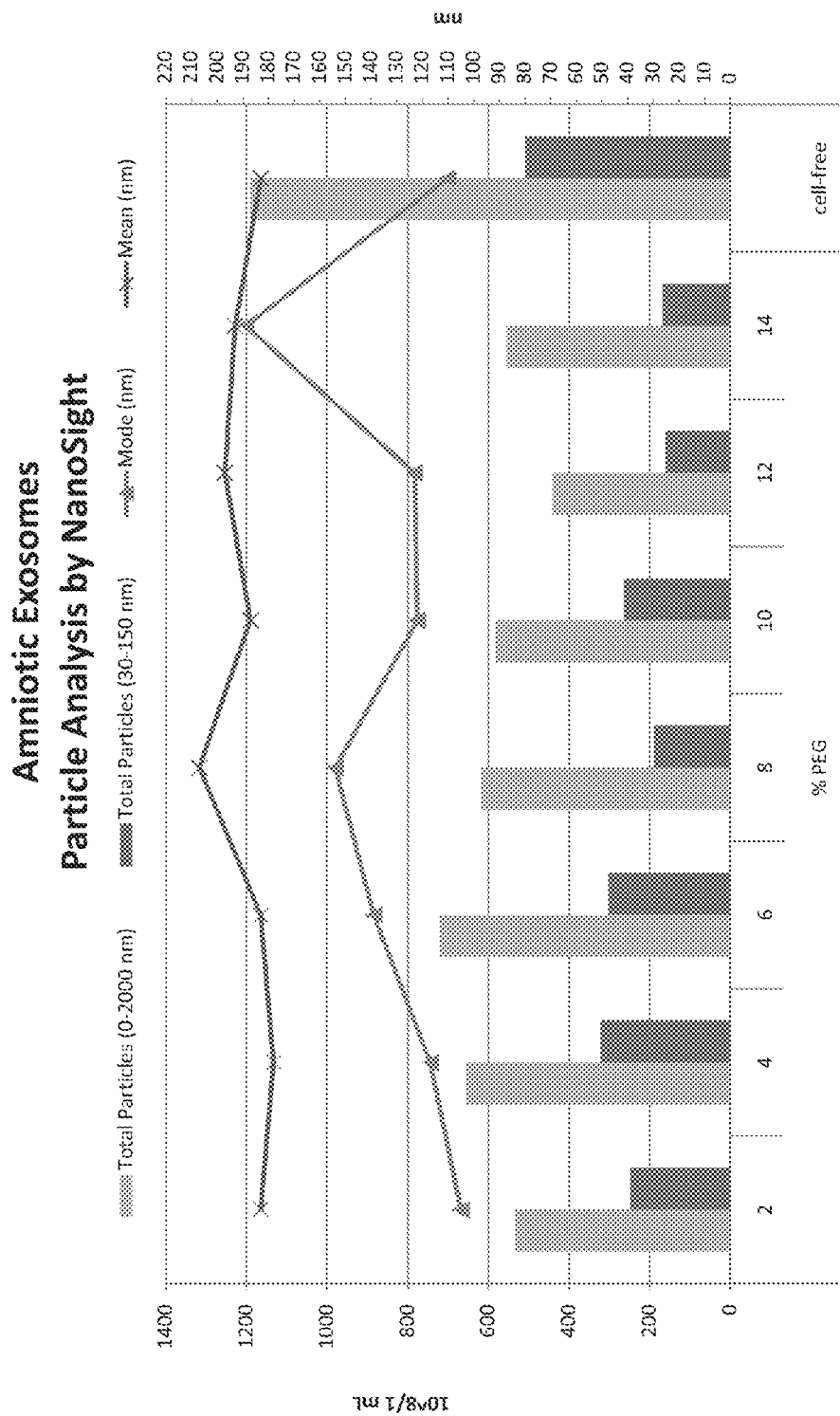
FIG. 14 Shows efficiency of exosomes recovery from amniotic fluid with PEG6000 of different percentages.

The results are shown in FIG. 14. PEG6000 at concentrations 2-14% allows very efficient recovery of exosomes from amniotic fluid. In this particular setting, the maximal recovery was accomplished with 4-6% PEG6000 (w/v).

Example 13

Recovery of Exosomes from Cerebrospinal Fluid (CSF) with 2-14% PEG6000

Exosomes were isolated from human cerebrospinal fluid (CSF): 1 mL CSF samples (after 30 min 2000 g centrifugation to remove cell debris) were combined with PEG6000 stock solution, resulting in 2%, 4%, 6%, 8%, 10%, 12% and 14% final PEG concentration (w/v). The samples (PEG6000+CSF) were carefully mixed and incubated at 4° C. for ~14 h, then the samples were spun down at 10,000 g for 1 h. The supernatant was discarded, and the exosome pellet was resuspended in PBS and the number of exosomes was quantified on a Nanosight LM10 instrument. The number of exosomes in the samples (30-150 nm size range) was compared to the number of nanoparticles in the same size range in the original CSF sample (subjected to 30 min 2000 g centrifugation to remove cell debris)—to analyze the efficiency of recovery. The entire population of nanoparticles in the size range 0-2000 nm was tracked as well.

Figure 15:
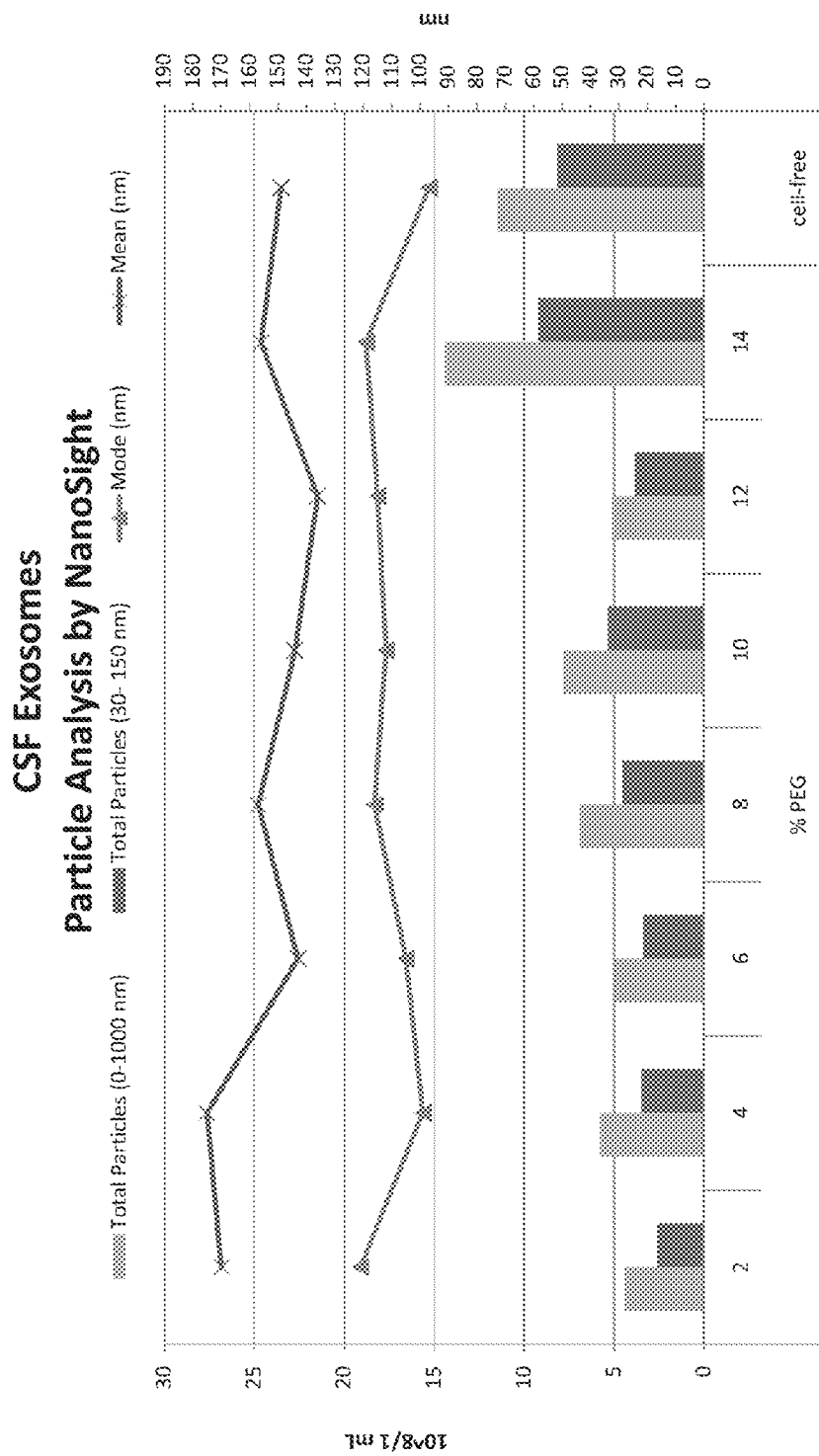
FIG. 15 Shows efficiency of exosomes recovery from cerebrospinal fluid (CSF) with PEG6000 of different percentages.

The results are shown in FIG. 15. PEG6000 at concentrations 2-14% allows very efficient recovery of exosomes from CSF. In this particular setting, the maximal recovery was accomplished with 8-14% PEG6000.

Example 14

Recovery of Exosomes from Plasma with 5% PEG6000 and Effects of Proteinase K on Removal of Protein from the Sample Exosomes were isolated from human plasma: 100 µL plasma samples from three healthy donors (after 30 min 2000 g centrifugation to remove cell debris) were combined with ⅕th volume of 30% (w/v) PEG6000 stock solution, resulting in 5% final PEG concentration. The samples (PEG6000+plasma) were carefully mixed and incubated at 4° C. for 30 min, then the samples were spun down at 10,000 g for 30 min. The supernatant was discarded, and the exosome pellet was resuspended in PBS and the number of exosomes was quantified on a Nano sight LM10 instrument.

Another set of 100 µL plasma samples from three healthy donors (after 30 min 2000 g centrifugation to remove cell debris) was treated with Proteinase K (in order to remove protein from the sample and thus enhance the purity of the exosomes), and then combined with ⅕th volume of 30% PEG6000 stock solution, resulting in 5% final PEG concentration—for precipitation of exosomes, following above protocol.

The number of exosomes in the samples (30-150 nm size range), obtained by Nanosight LM10 quantification, was compared to the number of nanoparticles in the same size range in the original plasma sample—to analyze the efficiency of recovery. Data for all samples were normalized for sample volume and dilution factor.

Figure 16:
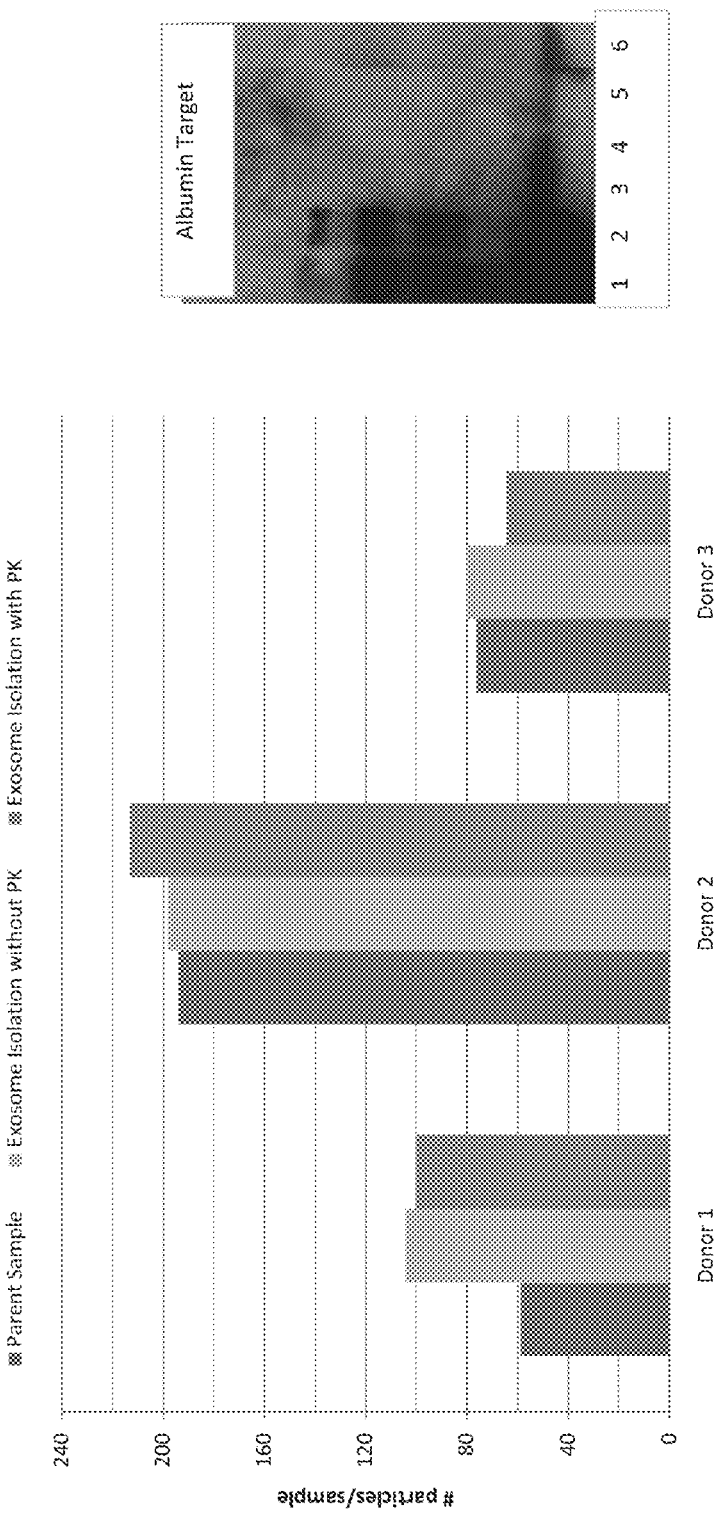
FIG. 16 Shows efficiency of exosomes recovery from plasma with 5% PEG6000 and effects of Proteinase K on removal of Albumin from the sample.

The results are shown in FIG. 16 (Left panel). For all three donors (donor 1, 2, 3) 5% PEG6000 allows very efficient, near quantitative, recovery of exosomes from plasma. Proteinase K treatment does not affect the number of exosomes recovered, but removes extracellular proteins that might be present at low levels in the preparations. All the proteins and protein complexes are typically below 20 nm in size, and thus undetectable with Nanosight instrument, which reliably measures only the larger nanoparticles, in the range 30-1000 nm. The fact that Proteinase K treatment did not result in reduction of the nanoparticle numbers provides additional proof that what was traced with the Nanosight LM10 instrument is truly of exosome origin, and not the protein complexes.

Next, the original plasma sample was treated with Proteinase K and compared to the untreated plasma sample by western blot analysis, using anti-Albumin antibodies—to monitor levels of Albumin, the major protein found in blood. The results are shown in FIG. 16 (Right panel). Lanes 1 and 2—untreated plasma samples; lanes 3-6: plasma treated with Proteinase K.

Results clearly indicate that proteinase K treatment allows elimination of the majority of protein from the plasma sample. With subsequent PEG precipitation, it would be possible to recover exosomes of higher purity, containing minimal—if any—protein contamination. This additional step of Proteinase K treatment might be utilized when ultra pure exosome preparations are required, and in case body fluids rich in protein content are utilized—thus making it challenging to recover clean exosome population.

Further exemplary embodiments are provided in the following numbered clauses.

1. A method for the isolation of exosomes from a biological fluid sample comprising:
a) adding a volume-excluding polymer to the biological fluid sample,
b) incubating the biological fluid sample with the volume-excluding polymer; and
d) isolating the precipitated exosomes from the biological fluid sample.

2. The method of clause 1, wherein the molecular weight of the volume-excluding polymer is from 1000 to 1,000,000 daltons.

3. The method of clause 2, wherein the molecular weight of the volume-excluding polymer is from 3000 to 10000 daltons.

4. The method of clause 3, wherein the molecular weight of the volume-excluding polymer is from 4000 to 8000 daltons.

5. The method of clause 4, wherein the concentration of volume-excluding polymer upon mixing with the biological fluid is from 1% to 90%.

6. The method of clause 5, wherein the concentration of volume-excluding polymer upon mixing with the biological fluid is from 3% to 15%.

7. The method of clause 6, wherein the concentration of volume-excluding polymer upon mixing with the biological fluid is from 4% to 12%.

8. The method of clause 1, further comprising the step of clarifying the biological fluid sample before adding the volume-excluding polymer.

9. The method of clause 1 further comprising the step of isolating nucleic acid and protein from the exosomes.

10. The method of clause 1, wherein the biological fluid is from prokaryotes, eukaryotes, bacteria, fungi, yeast, invertebrates, vertebrates, reptiles, fish, insects, plants or animals.

11. The method of clause 1, wherein the biological fluid is selected from the group consisting of blood serum, plasma, whole blood, urine, saliva, breast milk, tears, sweat, joint fluid, cerebrospinal fluid, semen, vaginal fluid, ascitic fluid, amniotic fluid, and cell culture media.

12. The method of clause 1, wherein the biological fluid sample is from a human.

13. The method of clause 1, further comprising fractionating the isolated exosomes.

14. The method of clause 1, wherein the volume-excluding polymer is polyethylene glycol, dextran, dextran sulfate, dextran acetate, polyvinyl alcohol, polyvinyl acetate, or polyvinyl sulfate.

15. The method of clause 14, wherein the volume-excluding polymer is polyethylene glycol.

16. The method of clause 1, further comprising contacting the biological fluid sample prior to the addition of the volume-excluding polymer with a protease, under conditions suitable for digestion of protein.

17. The method of clause 16, wherein the protease is proteinase K.

18. A method for the isolation of exosomes from a biological tissue sample comprising:
a) lysing the biological tissue sample,
b) clarifying the lysed sample
c) adding a volume-excluding polymer to the clarified sample,
d) incubating the clarified sample with the volume-excluding polymer, and
e) isolating the precipitated exosomes.

19. The method of clause 18, wherein the molecular weight of the volume-excluding polymer is from 1000 to 1,000,000 daltons.

20. The method of clause 19, wherein the molecular weight of the volume-excluding polymer is from 3000 to 10000 daltons.

21. The method of clause 20, wherein the molecular weight of the volume-excluding polymer is from 4000 to 8000 daltons.

22. The method of clause 18, wherein the concentration of volume-excluding polymer upon mixing with the biological sample is from 1% to 90%.

23. The method of clause 22, wherein the concentration of volume-excluding polymer upon mixing with the biological sample is from 3% to 15%.

24. The method of clause 23, wherein the concentration of volume-excluding polymer upon mixing with the biological sample is from 4% to 12%.

25. The method of clause 18, wherein the volume-excluding polymer is polyethylene glycol, dextran, dextran sulfate, dextran acetate, polyvinyl alcohol, polyvinyl acetate, or polyvinyl sulfate.

26. The method of clause 25, wherein the volume-excluding polymer is polyethylene glycol.

27. The method of clause 18 further comprising the step of isolating nucleic acid and protein from the exosomes.

28. The method of clause 18, wherein the biological sample is from prokaryotes, eukaryotes, bacteria, fungi, yeast, invertebrates, vertebrates, reptiles, fish, insects, plants or animals.

29. The method of clause 18, wherein the biological sample is selected from the group consisting of surgical samples, biopsy samples, tissues, feces, plant tissue, insect tissue, fungi, bacteria, parasites and cultured cells.

30. The method of clause 18, further comprising contacting the biological tissue sample with a protease, under conditions suitable for digestion of protein, prior to the addition of the volume-excluding polymer.

31. The method of clause 30, wherein the protease is proteinase K.

All publications, patents and patent applications mentioned in this Specification are indicative of the level of skill of those of ordinary skill in the art and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one of ordinary skill in the art are intended to be included within the scope of the following claims.

What is claimed is:

1. A method for the isolation of exosomes from a biological fluid sample comprising:
a) adding polyethylene glycol to the biological fluid sample,
b) incubating the biological fluid sample with the polyethylene glycol,
c) isolating the precipitated exosomes from the biological fluid sample; and
d) fractionating the isolated exosomes.

2. The method of claim 1, wherein the molecular weight of the polyethylene glycol is from 3000 to 20000 daltons.

3. The method of claim 2, wherein the molecular weight of the polyethylene glycol is from 4000 to 8000 daltons.

4. The method of claim 1, wherein the concentration of polyethylene glycol upon mixing with the biological fluid is from 3% to 15%.

5. The method of claim 4, wherein the concentration of polyethylene glycol upon mixing with the biological fluid is from 4% to 12%.

6. The method of claim 1, further comprising the step of clarifying the biological fluid sample before adding the polyethylene glycol.

7. The method of claim 1, further comprising the step of isolating nucleic acid from the exosomes.

8. The method of claim 1, wherein the biological fluid is from prokaryotes, eukaryotes, bacteria, fungi, yeast, invertebrates, vertebrates, reptiles, fish, insects, plants or animals.

9. The method of claim 1, wherein the biological fluid is selected from the group consisting of blood serum, plasma, whole blood, urine, saliva, breast milk, tears, sweat, joint fluid, cerebrospinal fluid, semen, vaginal fluid, ascitic fluid, amniotic fluid, and cell culture media.

10. The method of claim 1, wherein the biological fluid sample is from a human.

11. The method of claim 1, further comprising contacting the biological fluid sample prior to the addition of the polyethylene glycol with a protease, under conditions suitable for digestion of protein.

12. The method of claim 11, wherein the protease is proteinase K.

13. The method of claim 1 further comprising the step of isolating protein from the exosomes.

14. A method for the isolation of exosomes from a biological fluid sample comprising:
    a) contacting the biological fluid sample with a protease, under conditions suitable for digestion of protein,
    b) adding polyethylene glycol to the protease treated biological fluid sample,
    c) incubating the biological fluid sample with the polyethylene glycol; and
    d) isolating the precipitated exosomes from the biological fluid sample.

15. The method of claim 14, wherein the protease is proteinase K.

16. The method of claim 14, further comprising fractionating the isolated exosomes.

17. The method of claim 14, wherein the molecular weight of the polyethylene glycol is from 3000 to 20000 daltons.

18. The method of claim 14, wherein the concentration of polyethylene glycol upon mixing with the biological fluid is from 3% to 15%.

19. The method of claim 14, further comprising the step of clarifying the biological fluid sample before adding the polyethylene glycol.

20. The method of claim 14, further comprising the step of isolating nucleic acid from the exosomes.

* * * * *